United States Patent
Takada et al.

(10) Patent No.: US 12,343,211 B2
(45) Date of Patent: Jul. 1, 2025

(54) ULTRASOUND IMAGE ANALYZING APPARATUS FOR QUANTIFYING CONTRAST AGENT STAGNATION

(71) Applicant: CANON MEDICAL SYSTEMS CORPORATION, Otawara (JP)

(72) Inventors: Yuko Takada, Utsunomiya (JP); Masaki Watanabe, Utsunomiya (JP); Yasunori Honjo, Utsunomiya (JP); Yu Igarashi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 121 days.

(21) Appl. No.: 17/305,893

(22) Filed: Jul. 16, 2021

(65) Prior Publication Data

US 2021/0338207 A1 Nov. 4, 2021

Related U.S. Application Data

(63) Continuation of application No. PCT/JP2020/000286, filed on Jan. 8, 2020.

(30) Foreign Application Priority Data

Jan. 17, 2019 (JP) ................. 2019-006215

(51) Int. Cl.
 A61B 8/00  (2006.01)
 A61B 8/06  (2006.01)
(52) U.S. Cl.
 CPC ............. *A61B 8/5207* (2013.01); *A61B 8/06* (2013.01); *A61B 8/463* (2013.01); *A61B 8/481* (2013.01); *A61B 8/5253* (2013.01)
(58) Field of Classification Search
 None
 See application file for complete search history.

(56) References Cited

U.S. PATENT DOCUMENTS

2003/0125624 A1  7/2003  Shiki
2005/0131300 A1*  6/2005  Bakircioglu ............. A61B 8/06
  600/453

(Continued)

FOREIGN PATENT DOCUMENTS

JP  2003-061958 A  3/2003
JP  2009-119134 A  6/2009

(Continued)

OTHER PUBLICATIONS

Voorneveld et al., "Native blood speckle vs ultrasound contrast agent for particle image velocimetry with ultrafast ultrasound—in vitro experiments," (Sep. 2016) 2016 IEEE International Ultrasonics Symposium (IUS), Tours, France, 2016, pp. 1-4. (Year: 2016).*

(Continued)

*Primary Examiner* — Joel Lamprecht
*Assistant Examiner* — Ashish S Jasani
(74) *Attorney, Agent, or Firm* — Oblon, McClelland, Maier & Neustadt, L.L.P.

(57) ABSTRACT

An ultrasound diagnosis apparatus according to an embodiment includes processing circuitry. The processing circuitry is configured to generate contrast image data on the basis of a contrast signal acquired from an examined subject to whom a contrast agent is administered. The processing circuitry is configured to generate blood flow image data on the basis of a blood flow signal estimated by performing a filtering process on the contrast signal. The processing circuitry is configured to output information indicating a region where the contrast agent is stagnant within a region of interest, on the basis of the contrast image data and the blood flow image data.

16 Claims, 13 Drawing Sheets

(56) References Cited

U.S. PATENT DOCUMENTS

| | | | |
|---|---|---|---|
| 2005/0283075 A1* | 12/2005 | Ma | G06T 19/003 600/441 |
| 2006/0184032 A1 | 8/2006 | Shiki | |
| 2010/0069757 A1* | 3/2010 | Yoshikawa | A61B 5/02007 600/454 |
| 2011/0301457 A1* | 12/2011 | Yoshiara | A61B 8/08 600/431 |
| 2015/0141832 A1* | 5/2015 | Yu | A61B 8/488 600/455 |
| 2015/0245819 A1* | 9/2015 | Yoshiara | A61B 8/0866 600/431 |
| 2015/0257739 A1* | 9/2015 | Yao | A61B 8/0891 600/431 |
| 2015/0320395 A1 | 11/2015 | Sato | |
| 2017/0055956 A1 | 3/2017 | Osumi et al. | |
| 2018/0353158 A1* | 12/2018 | Frinking | G16H 50/30 |
| 2019/0223828 A1* | 7/2019 | Torp | A61B 8/5207 |
| 2019/0357874 A1 | 11/2019 | Yoshiara | |
| 2019/0365344 A1* | 12/2019 | Gu | A61B 8/085 |
| 2021/0145361 A1* | 5/2021 | del Alamo de Pedro | A61M 60/178 |

FOREIGN PATENT DOCUMENTS

| | | | |
|---|---|---|---|
| JP | 2011-254963 | A | 12/2011 |
| JP | 2014-138761 | A | 7/2014 |
| JP | 2014-158698 | A | 9/2014 |
| JP | 2017-042606 | A | 3/2017 |
| JP | 2018-015155 | A | 2/2018 |
| JP | 2019-202144 | A | 11/2019 |
| WO | WO 98/49940 | A1 | 11/1998 |
| WO | WO 2014/115782 | A1 | 7/2014 |

OTHER PUBLICATIONS

International Search Report issued Feb. 18, 2020 in PCT/JP2020/00286 filed on Jan. 8, 2020, 2 pages.
Office Action issued Nov. 8, 2022, in corresponding Japanese Patent Application No. 2019-006215 (with English Translation), 3 pages.
Extended European Search Report issued Aug. 16, 2022 in European Patent Application No. 20741871.6, 8 pages.
Combined Chinese Office Action and Search Report issued Jan. 30, 2024 in Chinese Patent Application No. 202080009358.4, 8 pages.
Japanese Office Action issued on May 9, 2023 in Japanese Patent Application No. 2019-006215, 4 pages.

* cited by examiner

ULTRASOUND IMAGE ANALYZING APPARATUS FOR QUANTIFYING CONTRAST AGENT STAGNATION

CROSS-REFERENCE TO RELATED APPLICATIONS

This application is a continuation of International Application No. PCT/JP2020/000286, filed on Jan. 8, 2020 which claims the benefit of priority of the prior Japanese Patent Application No. 2019-006215, filed on Jan. 17, 2019; the entire contents of all of which are incorporated herein by reference.

FIELD

Embodiments described herein relate to an image analyzing apparatus.

BACKGROUND

Conventionally, ultrasound diagnosis apparatuses implement imaging methods in accordance with various purposes. For example, an ultrasound diagnosis apparatus implements a contrast echo method called Contrast Harmonic Imaging (CHI). According to a CHI method, for example, imaging is performed by injecting a contrast agent through a vein, to examine the heart, the liver, or the like.

Contrast-enhanced images (hereinafter, "contrast images") obtained by CHI primarily render blood vessels in examined subjects. In some situations, however, contrast images also render a contrast agent leaking from a blood vessel and being stagnant in a tissue as a result of being captured in Kupffer cells or the like.

DETAILED DESCRIPTION

An ultrasound diagnosis apparatus according to an embodiment includes processing circuitry. The processing circuitry is configured to generate contrast image data on the basis of a contrast signal acquired from an examined subject to whom a contrast agent is administered. The processing circuitry is configured to generate blood flow image data on the basis of a blood flow signal estimated by performing a filtering process on the contrast signal. The processing circuitry is configured to output information indicating a region where the contrast agent is stagnant within a region of interest, on the basis of the contrast image data and the blood flow image data.

An image analyzing apparatus according to embodiments will be explained below, with reference to the drawings. Possible embodiments are not limited to the embodiments described below. Further, the description of each of the embodiments is, in principle, similarly applicable to any other embodiment.

First Embodiment

Figure 1:
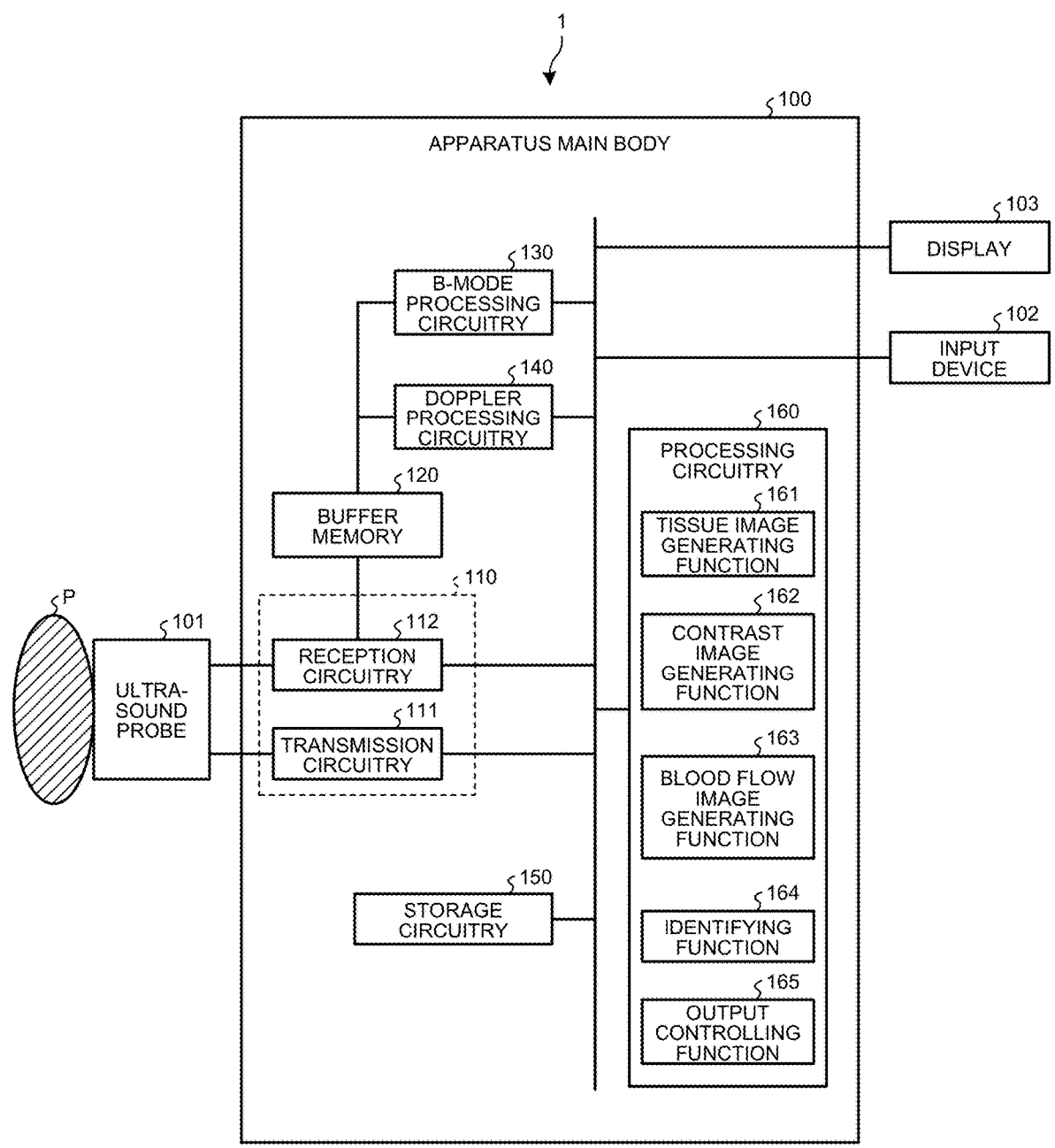
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input device 102, and a display 103.

For example, the ultrasound probe 101 includes a plurality of elements such as piezoelectric transducer elements. Each of the plurality of elements is configured to generate an ultrasound wave on the basis of a drive signal supplied thereto from transmission circuitry 111 of transmission and reception circuitry 110 included in the apparatus main body 100. Further, the ultrasound probe 101 is configured to receive reflected waves from an examined subject (hereinafter "patient") P and to convert the received reflected waves into electric signals. Further, the ultrasound probe 101 includes, for example, a matching layer provided for the piezoelectric transducer elements, as well as a backing member or the like that prevents the ultrasound waves from propagating rearward from the piezoelectric transducer elements. In this situation, the ultrasound probe 101 is detachably connected to the apparatus main body 100.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected-wave signal by each of the plurality of elements included in the ultrasound probe 101. The amplitude of the received reflected-wave signal is dependent on the difference between the acoustic impedances on the surface of discontinuity on which the ultrasound wave is reflected. When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction. Further, the ultrasound probe 101 is configured to output the reflected-wave signals to reception circuitry 112 of the transmission and reception circuitry 110 (explained later).

The ultrasound probe 101 is provided so as to be attachable to and detachable from the apparatus main body 100. When a two-dimensional region inside the patient P is to be scanned (a two-dimensional scan), an operator connects, for example, a one-dimensional (1D) array probe in which the plurality of piezoelectric transducer elements are arranged in a row to the apparatus main body 100, as the ultrasound probe 101. The 1D array probe may be a linear-type ultrasound probe, a convex-type ultrasound probe, a sector-type ultrasound probe, or the like. Further, when a three-dimensional region inside the patient P is to be scanned (a tree-dimensional scan), the operator connects, for example, a mechanical four-dimensional (4D) probe or a two-dimensional (2D) probe to the apparatus main body 100, as the ultrasound probe 101. The mechanical 4D probe is capable of performing the two-dimensional scan by using the plurality of piezoelectric transducer elements arranged in a row like in the 1D array probe and is also capable of performing the three-dimensional scan by causing the plurality of piezoelectric transducer elements to swing with a predetermined angle (a swinging angle). Further, the 2D array probe is capable of performing the three-dimensional scan by using the plurality of piezoelectric transducer elements arranged in a matrix formation and is also capable of performing the two-dimensional scan by transmitting ultrasound waves in a converged manner.

For example, the input device 102 is realized by input means such as a mouse, a keyboard, a button, a panel switch, a touch command screen, a foot switch, a trackball, a joystick, and/or the like. The input device 102 is configured to receive various types of setting requests from the operator of the ultrasound diagnosis apparatus 1 and to transfer the received various types of setting requests to the apparatus main body 100.

The display 103 is configured to display a Graphical User Interface (GUI) used by the operator of the ultrasound diagnosis apparatus 1 for inputting the various types of setting requests via the input device 102 and to display an ultrasound image represented by ultrasound image data generated by the apparatus main body 100, and the like. The display 103 is realized by using a liquid crystal monitor, a Cathode Ray Tube (CRT) monitor, or the like.

The apparatus main body 100 is configured to generate the ultrasound image data on the basis of the reflected-wave signals received by the ultrasound probe 101. The ultrasound image data is an example of image data. The apparatus main body 100 is capable of generating two-dimensional ultrasound image data on the basis of reflected-wave data corresponding to a two-dimensional region of the patient P and being received by the ultrasound probe 101. Further, the apparatus main body 100 is capable of generating three-dimensional ultrasound image data on the basis of reflected-wave data corresponding to a three-dimensional region of the patient P and being received by the ultrasound probe 101.

As illustrated in FIG. 1, the apparatus main body 100 includes the transmission and reception circuitry 110, a buffer memory 120, B-mode processing circuitry 130, Doppler processing circuitry 140, storage circuitry 150, and processing circuitry 160.

Under control of the processing circuitry 160, the transmission and reception circuitry 110 is configured to cause the ultrasound probe 101 to transmit ultrasound waves and to cause the ultrasound probe 101 to receive ultrasound waves (reflected waves of the ultrasound waves). In other words, the transmission and reception circuitry 110 is configured to perform an ultrasound scan (an ultrasound wave scan) via the ultrasound probe 101. The transmission and reception circuitry 110 is an example of the transmission and reception unit. The transmission and reception circuitry 110 includes the transmission circuitry 111 and the reception circuitry 112.

Under control of the processing circuitry 160, the transmission circuitry 111 is configured to cause the ultrasound probe 101 to transmit the ultrasound waves. The transmission circuitry 111 includes a rate pulser generating circuit, a transmission delay circuit, and a transmission pulser and is configured to supply the drive signal to the ultrasound probe 101. When a two-dimensional region inside the patient P is to be scanned (is subject to a scan), the transmission circuitry 111 causes the ultrasound probe 101 to transmit an ultrasound beam for scanning the two-dimensional region. Further, when a three-dimensional region inside the patient P is to be scanned, the transmission circuitry 111 causes the ultrasound probe 101 to transmit an ultrasound beam for scanning the three-dimensional region.

The rate pulser generating circuit is configured to repeatedly generate a rate pulse for forming a transmission ultrasound wave (a transmission beam) at a predetermined rate frequency (i.e., a Pulse Repetition Frequency [PRF]). As a result of the rate pulse being routed through the transmission delay circuit, voltage is applied to the transmission pulser with various transmission delay time periods. For example, the transmission delay circuit is configured to apply a transmission delay time period that is required to converge the ultrasound waves generated by the ultrasound probe 101 into the form of a beam and to determine transmission directionality and that corresponds to each of the piezoelectric transducer elements, to each of the rate pulses generated by the rate pulser generating circuit. The transmission pulser is configured to apply the drive signal (a drive pulse) to the ultrasound probe 101 with timing based on the rate pulses. In this situation, by varying the transmission delay time periods applied to the rate pulses, the transmission delay circuit is able to arbitrarily adjust the transmission directions of the ultrasound waves transmitted from the surfaces of the piezoelectric transducer elements.

The drive pulse from the transmission pulser reaches the piezoelectric transducer elements in the ultrasound probe 101 via a cable and is subsequently converted from an electric signal into mechanical vibration at the piezoelectric transducer elements. The ultrasound wave generated by the mechanical vibration is transmitted to the inside of the patient's body. In this situation, the ultrasound waves having the transmission delay time periods varied in correspondence with the piezoelectric transducer elements are converged to be propagated in a predetermined direction.

Under control of the processing circuitry 160, the transmission circuitry 111 has a function that is able to instantly change transmission frequency, transmission drive voltage, and the like, for the purpose of executing a predetermined scan sequence. In particular, the function to change the transmission drive voltage is realized by using a linear-amplifier-type transmission circuit of which the value can be instantly switched or by using a mechanism configured to electrically switch between a plurality of power source units.

The reflected waves of the ultrasound waves transmitted by the ultrasound probe 101 reach the piezoelectric transducer elements inside the ultrasound probe 101 and are subsequently converted from the mechanical vibration to electric signals (reflected-wave signals) at the piezoelectric transducer elements, before being input to the reception circuitry 112. The reception circuitry 112 includes a pre-amplifier, an Analog-to-Digital (A/D) converter, a quadrature detecting circuit, and the like and is configured to generate the reflected-wave data by performing various types of processes on the reflected-wave signals received by the ultrasound probe 101. Further, the reception circuitry 112 is configured to store the generated reflected-wave data into the buffer memory 120.

The pre-amplifier is configured to amplify the reflected-wave signals for each of the channels and to perform a gain adjusting process (a gain correction). The A/D converter is configured to convert the gain-corrected reflected-wave signals into digital signals by performing an A/D conversion on the gain-corrected reflected-wave signals. The quadrature detecting circuit is configured to convert the reflected-wave signals resulting from the A/D conversion into an In-phase signal (an I signal) and a Quadrature-phase signal (a Q signal) that are in a baseband. Further, the quadrature detecting circuit is configured to store the I signal and the Q signal (IQ signals) into the buffer memory 120 as the reflected-wave data.

The reception circuitry 112 is configured to generate two-dimensional reflected-wave data from two-dimensional reflected-wave signals received by the ultrasound probe 101. Further, the reception circuitry 112 is configured to generate three-dimensional reflected-wave data from three-dimensional reflected-wave signals received by the ultrasound probe 101.

In this situation, the ultrasound diagnosis apparatus 1 according to the present embodiment is configured to display a blood flow image indicating blood flow information, a contrast image rendering a tissue perfusion of very small capillary blood vessels and the like by using a contrast agent, and a tissue image indicating a tissue shape. The blood flow image is an image represented by color Doppler image data, which is blood flow image data. The contrast image is an image represented by B-mode imaged data, which is contrast image data. The tissue image is an image represented by B-mode image data, which is tissue image data.

Further, to realize the display, the transmission and reception circuitry 110 is configured to perform an ultrasound scan (a first ultrasound scan) to acquire the blood flow image data in a Doppler mode and to perform an ultrasound scan (a second ultrasound scan) to acquire the tissue image data and the contrast image data in a B-mode. The first ultrasound scan is an ultrasound scan performed on a region (a first scan region) inside the patient P injected with a contrast agent and is an ultrasound scan to obtain the blood flow information in the first scan region. The second ultrasound scan is an ultrasound scan performed to obtain information about the tissue shape and information about the tissue perfusion of small capillary blood vessels and the like, in a region (a second scan region) in the patient P.

In other words, to acquire the tissue image data and the contrast image data, the transmission and reception circuitry 110 performs the single second ultrasound scan, instead of performing ultrasound scans separately for acquiring the tissue image and for acquiring the contrast image. In other words, the ultrasound diagnosis apparatus 1 is able to acquire the three types of images, namely, the blood flow image, the tissue image, and the contrast image, as a result of the transmission and reception circuitry 110 simply performing the two types of ultrasound scans, namely, the first ultrasound scan and the second ultrasound scan.

It is sufficient when the first scan region and the second scan region overlap each other at least partially. The range of the first scan region and the range of the second scan region may be the same as each other. The range of the first scan region may be smaller than the range of the second scan region. Conversely, the range of the second scan region may be smaller than the range of the first scan region.

The buffer memory 120 is a memory configured to temporarily store therein the reflected-wave data generated by the transmission and reception circuitry 110. For example, the buffer memory 120 is configured to store therein reflected-wave data corresponding to a number of frames or reflected-wave data corresponding to a number of volumes. For example, under control of the reception circuitry 112, the buffer memory 120 stores therein reflected-wave data corresponding to a predetermined number of frames. Further, when reflected-wave data corresponding to one frame is newly generated by the reception circuitry 112, while having stored therein the reflected-wave data corresponding to the predetermined number of frames, the buffer memory 120 discards the reflected-wave data corresponding to one frame that was generated earliest and stores therein the newly-generated reflected-wave data corresponding to the one frame, under the control of the reception circuitry 112. For example, the buffer memory 120 is realized by using a semiconductor memory element such as a Random Access Memory (RAM), a flash memory, or the like.

The B-mode processing circuitry 130 and the Doppler processing circuitry 140 are signal processing units configured to read the reflected-wave data from the buffer memory 120 and to perform various types of signal processing processes on the read reflected-wave data.

The B-mode processing circuitry 130 is configured to generate data (B-mode data) in which the signal intensity (amplitude intensity) at each sampling point is expressed with a degree of brightness, by performing a logarithmic amplification and an envelope detecting process or the like on the reflected-wave data read from the buffer memory 120. The B-mode processing circuitry 130 is configured to output the generated B-mode data to the processing circuitry 160. For example, the B-mode processing circuitry 130 is realized by using a processor.

In this situation, the B-mode processing circuitry 130 is capable of varying the frequency band to be rendered in pictures, by varying the detected frequency. By using this function of the B-mode processing circuitry 130, the ultrasound diagnosis apparatus 1 according to the first embodiment is capable of implementing Contrast Harmonic Imaging (CHI) by which non-linear signals from the contrast agent are rendered in pictures. For example, the B-mode processing circuitry 130 is capable of generating B-mode data (second B-mode data) from which contrast image data is to be derived. Specific processes performed by the B-mode processing circuitry 130 according to the first embodiment will be explained in detail later.

By performing a frequency analysis on the reflected-wave data read from the buffer memory 120, the Doppler processing circuitry 140 is configured to extract motion information of moving members (blood flows, tissues, contrast agent echo components, and the like) based on the Doppler effect and to generate data (Doppler data) indicating the extracted motion information. For example, the Doppler processing circuitry 140 extracts an average velocity value, an average dispersion value, an average power value, and the like with respect to a large number of points as the motion information of the moving members and generates Doppler data indicating the extracted motion information of the moving members. The Doppler processing circuitry 140 is configured to output the generated Doppler data to the processing circuitry 160.

By using the abovementioned function of the Doppler processing circuitry 140, the ultrasound diagnosis apparatus 1 according to the first embodiment is capable of implementing a color Doppler method that may be called Color Flow Mapping (CFM) method. According to the color flow mapping method, the ultrasound waves are transmitted and received multiple times on a plurality of scanning lines. Further, a signal derived from the blood flow is extracted from a data sequence in mutually the same position, while suppressing a signal (a clutter signal) derived from a stationary or slow-moving tissue, by applying a Moving Target Indicator (MTI) filter to the data sequence in mutually the same position. Further, according to the color flow mapping method, blood flow information, such as velocity of the blood flow, dispersion of the blood flow, power of the blood flow, and the like, is estimated from the blood flow signal. The processing circuitry 160 (explained later) is configured to generate ultrasound image data (blood flow image data: color Doppler image data) that, for example, two-dimensionally displays, in color, a distribution of estimated results of the blood flow information. Further, the display 103 is configured to display a blood flow image represented by the blood flow image data.

As the MTI filter, the Doppler processing circuitry 140 according to the present embodiment is configured to employ an adaptive MTI filter that varies a coefficient thereof in accordance with an input signal. For example, as the adaptive MTI filter, the Doppler processing circuitry 140 employs a filter called "eigenvector regression filter". The "eigenvector regression filter", which is an adaptive MTI filter using eigenvectors, will hereinafter be referred to as an "eigenvector MTI filter".

The eigenvector MTI filter is configured to calculate eigenvectors from a correlation matrix and to calculate a coefficient used for a clutter component suppressing process from the calculated eigenvectors. This method is an application of a method used in a principal component analysis, a Karhunen-Loeve transform, or an eigenspace method.

The Doppler processing circuitry 140 according to the first embodiment that employs the eigenvector MTI filter is configured to calculate a correlation matrix of the first scan region from a data sequence of successive pieces of reflected-wave data in mutually the same position (the same sampling point). Further, the Doppler processing circuitry 140 is configured to calculate eigenvalues of the correlation matrix and eigenvectors corresponding to the eigenvalues. Further, the Doppler processing circuitry 140 is configured to calculate a matrix obtained by reducing the rank of a matrix in which the eigenvectors are arranged on the basis of the magnitudes of the eigenvalues, as a filter matrix used for suppressing the clutter component.

Further, by using the filter matrix, the Doppler processing circuitry 140 is configured to identify a data sequence extracting the blood flow signal derived from the blood flow while suppressing the clutter component, from the data sequence of the successive pieces of reflected-wave data in mutually the same position (the same sampling point). Further, the Doppler processing circuitry 140 is configured to estimate blood flow information by performing a calculation such as an auto-correlation calculation while using the identified data sequence. Further, the Doppler processing circuitry 140 is configured to output Doppler data indicating the estimated blood flow information, to the processing circuitry 160. Specific processes performed by the Doppler processing circuitry 140 according to the first embodiment will be explained in detail later. The Doppler processing circuitry 140 is realized, for example. by using a processor. The Doppler processing circuitry 140 is an example of a blood flow information obtaining unit.

The B-mode processing circuitry 130 and the Doppler processing circuitry 140 are capable of processing both two-dimensional reflected-wave data and three-dimensional reflected-wave data.

The storage circuitry 150 is configured to store therein a control program for performing the ultrasound transmission and reception processes, image processing processes, and display processes, as well as diagnosis information (e.g., patients' IDs and observations of medical doctors) and various types of data such as diagnosis protocols, various types of body marks, and the like. For example, the storage circuitry 150 is realized by using a semiconductor memory element such as a RAM or a flash memory, a hard disk, or an optical disk.

For example, the storage circuitry 150 is configured to store therein various types of image data generated by the processing circuitry 160. Further, the storage circuitry 150 is also configured to store therein the data generated by the B-mode processing circuitry 130 and the Doppler processing circuitry 140. After a diagnosis process, for example, the operator is able to invoke any of the B-mode data and the Doppler data stored in the storage circuitry 150. The invoked data can serve as display-purpose ultrasound image data after being routed through the processing circuitry 160.

The processing circuitry 160 is configured to control the entirety of the processes performed by the ultrasound diagnosis apparatus 1. More specifically, the processing circuitry 160 is configured to control processes of the transmission and reception circuitry 110, the B-mode processing circuitry 130, and the Doppler processing circuitry 140, on the basis of the various types of setting requests input by the operator via the input device 102, and any of the various types of control programs and the various types of data read from the storage circuitry 150. Further, the processing circuitry 160 is configured to control the display 103 so as to display ultrasound images represented by the display-purpose ultrasound image data stored in the storage circuitry 150. The processing circuitry 160 is realized, for example, by using a processor. The ultrasound images are examples of images.

Further, the processing circuitry 160 is configured to control ultrasound scans by controlling the ultrasound probe 101 via the transmission and reception circuitry 110. For example, the processing circuitry 160 controls the first ultrasound scan and the second ultrasound scan described above.

The processing circuitry 160 is configured to generate the ultrasound image data from the data output by the B-mode processing circuitry 130 and the Doppler processing circuitry 140. The processing circuitry 160 generates two-dimensional B-mode image data in which the intensities of the reflected waves are expressed with brightness levels, from the two-dimensional B-mode data generated by the B-mode processing circuitry 130. Further, the processing circuitry 160 generates two-dimensional Doppler image data in which the blood flow information is rendered in pictures, from the two-dimensional Doppler data generated by the Doppler processing circuitry 140. The two-dimensional Doppler image data is velocity image data, dispersion image data, power image data, or image data combining any of these types of image data. As Doppler image data, the processing circuitry 160 generates blood flow image data in which the blood flow information is displayed in color or generates blood flow image data in which one piece of blood flow information is displayed in a gray scale, from the Doppler data serving as the blood flow information. The processing circuitry 160 is realized by using a processor.

In this situation, generally speaking, the processing circuitry 160 converts (by performing a scan convert process) a scanning line signal sequence from an ultrasound scan into a scanning line signal sequence in a video format used by, for example, television and generates the display-purpose ultrasound image data. For example, the processing circuitry 160 generates the display-purpose ultrasound image data by performing a coordinate transformation process in accordance with the ultrasound scanning mode used by the ultrasound probe 101. Further, as various types of image processing processes besides the scan convert process, the processing circuitry 160 performs, for example, an image processing process (a smoothing process) to re-generate an average brightness value image, an image processing process (an edge enhancement process) that uses a differential filter inside an image, or the like, by using a plurality of image frames resulting from the scan convert process. Also, the processing circuitry 160 combines text information of various types of parameters, scale graduations, body marks, and the like with the ultrasound image data.

Further, the processing circuitry 160 is configured to generate three-dimensional B-mode image data by performing a coordinate transformation process on three-dimensional B-mode data generated by the B-mode processing circuitry 130. Further, the processing circuitry 160 is configured to generate three-dimensional Doppler image data by performing a coordinate transformation process on three-dimensional Doppler data generated by the Doppler processing circuitry 140. In other words, the processing circuitry 160 generates the "three-dimensional B-mode image data and three-dimensional Doppler image data" as "three-dimensional ultrasound image data (volume data)". Further, the processing circuitry 160 is configured to perform any of various types of rendering processes on the volume data, to generate various types of two-dimensional image data for the purpose of displaying the volume data on the display 103.

Examples of the rendering processes performed by the processing circuitry 160 include a process of generating Multi Planar Reconstruction (MPR) image data from the volume data, by implementing an MPR method. Further, examples of the rendering processes performed by the processing circuitry 160 also include a Volume Rendering (VR) process to generate two-dimensional image data reflecting three-dimensional information. The processing circuitry 160 is an example of an image generating unit.

The B-mode data and the Doppler data are each ultrasound image data before the scan convert process. The data generated by the processing circuitry 160 is the display-purpose ultrasound image data after the scan convert process. The B-mode data and the Doppler data may be referred to as raw data.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processors realize the functions by reading and executing the programs saved in storage circuitry 150. Instead of saving the programs in the storage circuitry 150, it is also acceptable to directly incorporate the programs into the circuits of the processors. In that situation, the processors realize the functions by reading and executing the programs incorporated in the circuits thereof. Further, the processors of the present embodiments do not each necessarily have to be configured as a single circuit. It is also acceptable to structure one processor by combining together two or more independent circuits so as to realize the functions thereof. Further, two or more of the constituent elements illustrated in FIG. 1 may be integrated into one processor so as to realize the functions thereof.

An overall configuration of the ultrasound diagnosis apparatus 1 according to the first embodiment has thus been explained.

Incidentally, in Contrast Harmonic Imaging (CHI), contrast agents may, in some situations, leak from blood vessels and become stagnant in a tissue. Because it is difficult to visually distinguish the location where the contrast agent is stagnant from the location where the contrast agent is flowing (i.e., blood vessels), it is difficult to understand hemodynamics. Further, to determine whether a tumor occurring in a breast is benign or malignant, homogeneity of a contrast agent stagnant location in the tumor may be used in some situations.

Accordingly, to analyze stagnant locations of a contrast agent, the ultrasound diagnosis apparatus 1 according to the first embodiment is configured to execute the following processing functions. More specifically, in the ultrasound diagnosis apparatus 1, the processing circuitry 160 executes a tissue image generating function 161, a contrast image generating function 162, a blood flow image generating function 163, an identifying function 164, and an output controlling function 165. The tissue image generating function 161 is an example of a tissue image generating unit. The contrast image generating function 162 is an example of the contrast image generating unit. The blood flow image generating function 163 is an example of the blood flow image generating unit. The identifying function 164 is an example of the identifying unit. The output controlling function 165 is an example of the output controlling unit.

The tissue image generating function 161, the contrast image generating function 162, and the blood flow image generating function 163 according to the first embodiment are configured to generate various types of ultrasound image data, on the basis of signals acquired in ultrasound scans performed by the transmission and reception circuitry 110.

The transmission and reception circuitry 110 is configured to perform, via the ultrasound probe 101, a complex ultrasound scan in which the first ultrasound scans and the second ultrasound scans are alternately performed. Further, the scanning mode of the first ultrasound scans is a scanning mode in which the ultrasound transmission and reception is performed once for each scanning line in the first scan region formed with a plurality of scanning lines. By using this scanning mode, it is possible to enhance framerates. In the following sections, the first ultrasound scan will be referred to as a "high framerate ultrasound scan", while a CFM method implemented by performing the "high framerate ultrasound scan" will be referred to as a "high framerate method".

In this regard, according to a normal color Doppler method, the ultrasound transmission and reception is performed multiple times in mutually the same direction, so as to extract a blood flow signal from signals received thereby. The data sequence of reflected-wave signals (reflected-wave data) from mutually the same position that is obtained from the ultrasound transmission and reception is called a packet. The packet size denotes the number of times the ultrasound transmission and reception is performed in mutually the same direction, to obtain the blood flow information in one frame. The packet size according to a commonly-used color Doppler method is approximately 5 to 16. Capabilities of eigenvector MTI filters improve when the packet size is larger. However, when the packet size is increased, the framerate becomes lower.

Further, by using the high framerate method, it is possible to process the data sequences in mutually the same position among frames, in the frame direction (a time direction). For example, by using the high framerate method, it is possible to realize an MTI filter process as a process performed on data of an infinite length, from the data processing performed on the packet having a finite length. Consequently, as a result of improving the capabilities of the MTI filter by using the high framerate method, it becomes possible to also detect blood flow information related to blood flows having low flow rates. It also becomes possible to display a blood flow image indicating the blood flow information at a high framerate.

Together with the first ultrasound scans using the high framerate ultrasound scan, the processing circuitry 160 according to the first embodiment implements the second ultrasound scans in a scanning mode explained below.

The processing circuitry 160 divides the second scan region into a plurality of sectional regions and causes the ultrasound probe 101 to perform the second ultrasound scan on each of the plurality of sectional regions in-between the first ultrasound scans in a time-division manner. In other words, the transmission and reception circuitry 110 alternately performs, via the ultrasound probe 101, the first ultrasound scans and the second ultrasound scans performed on the plurality of sectional regions into which the second scan region is divided. Accordingly, in the first embodiment, the transmission and reception circuitry 110 performs the second ultrasound scans in-between the first ultrasound scans, so as to complete the second ultrasound scans corresponding to one frame in the time period of the first ultrasound scans corresponding to a number of frames. By using this scanning mode, the ultrasound diagnosis apparatus 1 according to the first embodiment is able to set ultrasound transmission and reception conditions (image quality conditions) independently for the first ultrasound scans and the for the second ultrasound scans.

Figure 2:
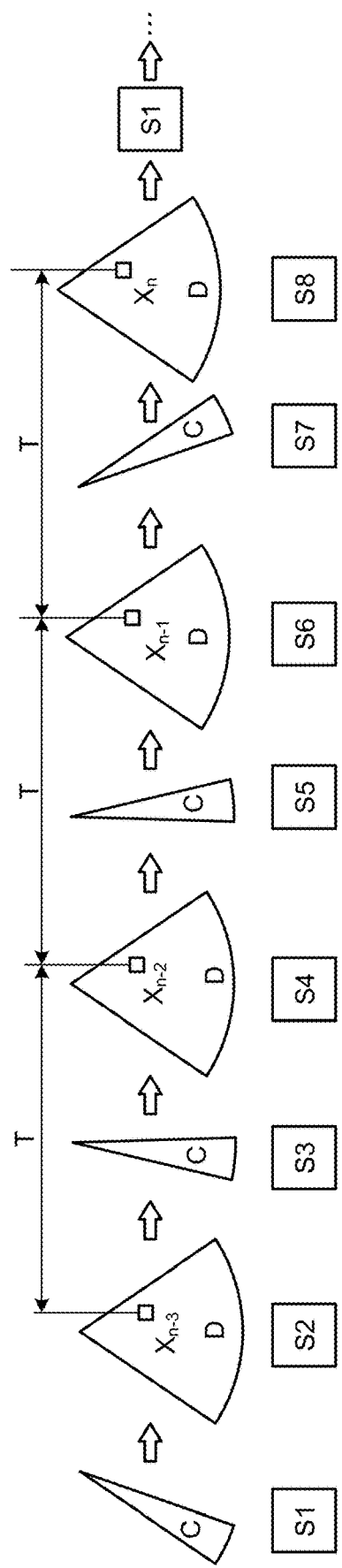
FIG. 2 is a drawing for explaining examples of first ultrasound scans and second ultrasound scans according to the first embodiment.
Figure 3:
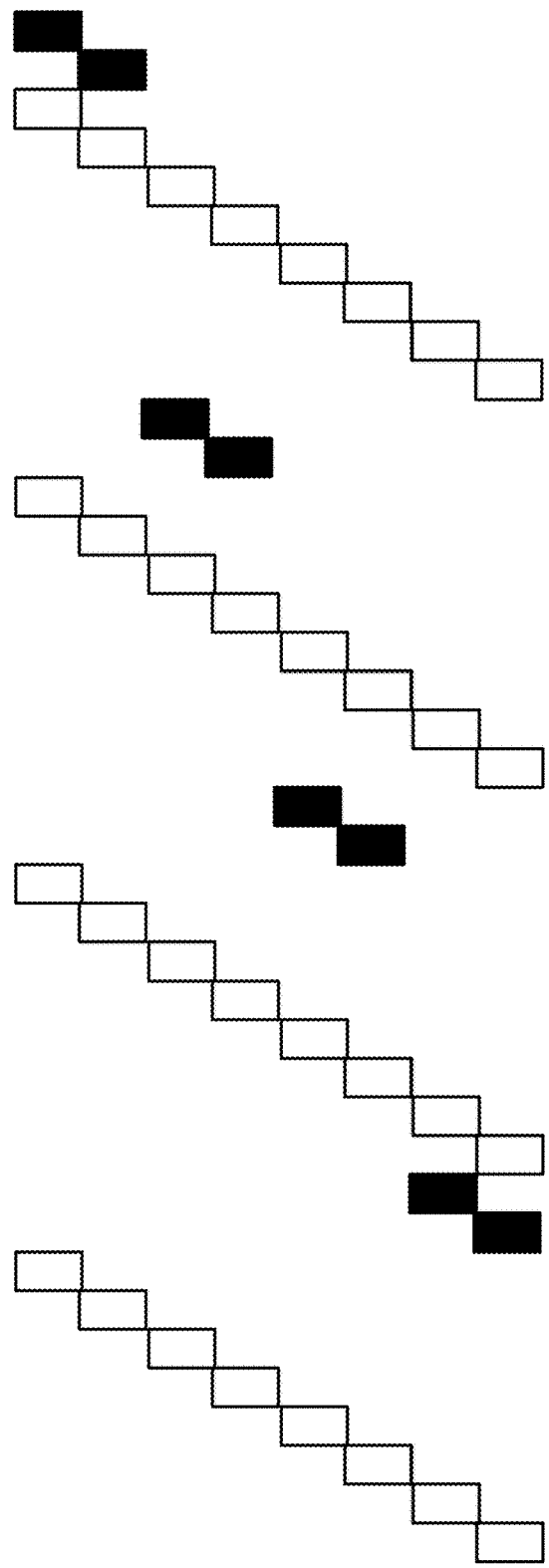
FIG. 3 is another drawing for explaining the examples of the first ultrasound scans and the second ultrasound scans according to the first embodiment.

The first ultrasound scans and the second ultrasound scans will be explained. FIGS. 2 and 3 are drawings for explaining examples of the first ultrasound scans and the second ultrasound scans according to the first embodiment. As illustrated in FIG. 2, the processing circuitry 160 divides the second scan region into four sectional regions (first to fourth sectional regions), on the basis of an instruction from the operator, information in an initial setting, or the like. The letter "C" in FIG. 2 denotes the sectional regions in which the second ultrasound scans are performed by using transmission and reception conditions for contrast harmonic imaging in a B-mode. Each of the sectional regions is formed by at least one scanning line.

For example, in the present embodiment, a Phase Modulation (PM) method may be implemented in the second ultrasound scans. The phase modulation method is a method by which, for example, two types of ultrasound waves in mutually-different phases are transmitted with respect to each of the scanning lines structuring a scanned range, so as to add together pieces of reflected-wave data based on reflected waves of the two types of ultrasound waves. In the present embodiment, when the phase modulation method is used, the transmission and reception circuitry 110 transmits the two types of ultrasound waves in the mutually-different phases with respect to each of the scanning lines structuring a sectional region, so that the B-mode processing circuitry 130 adds together the pieces of reflected-wave data based on the reflected waves of the two types of ultrasound waves. When the phase modulation method is used, the second ultrasound scans include the transmission and reception of each of the two types of ultrasound waves in the mutually-different phases.

Alternatively, in the second ultrasound scans, an Amplitude Modulation (AM) method may be used. The amplitude modulation method is a method by which, for example, three ultrasound waves modulated to have an amplitude ratio of "1:2:1" in mutually the same phase are transmitted with respect to each of the scanning lines structuring a scanned range, so as to perform an adding/subtracting process on pieces of reflected-wave data based on the reflected waves of the three ultrasound waves. In the present embodiment, when the amplitude modulation method is used, the transmission and reception circuitry 110 transmits an ultrasound wave of which the amplitude is "0.5", another ultrasound wave of which the amplitude is "1", and yet another ultrasound wave of which the amplitude is "0.5" in the stated order, with respect to each of the scanning lines structuring a sectional region. In other words, the transmission and reception circuitry 110 transmits the two type of ultrasound waves having the mutually-different amplitude levels. Further, the B-mode processing circuitry 130 performs an adding/subtracting process on the pieces of reflected-wave data based on the reflected waves of the three ultrasound waves (the two types of ultrasound waves). When the amplitude modulation method is used, the second ultrasound scans include the transmission and reception of each of the two types of ultrasound waves having the mutually-different amplitude levels.

For the second ultrasound scans, the operator may select which of the two methods is to be used, between the phase modulation method and the amplitude modulation method. For example, the phase modulation method has characteristics where it is possible to obtain an ultrasound image having a relatively high spatial resolution, because the transmission ultrasound waves have a relatively high frequency, but penetration is not excellent. In contrast, the amplitude modulation method has characteristics where penetration is excellent because the transmission ultrasound waves have a relatively low frequency, but the spatial resolution of the ultrasound image is relatively low. While taking these characteristics into consideration, the operator selects between the phase modulation method and the amplitude modulation method, by operating the input device 102.

For example, when the operator has selected the phase modulation method, the processing circuitry 160 stores information "0" indicating the phase modulation method into a predetermined region within the entire storage region of the storage circuitry 150. In contrast, when the operator has selected the amplitude modulation method, the processing circuitry 160 stores information "1" indicating the amplitude modulation method into the predetermined region of the storage circuitry 150. Further, the processing circuitry 160 refers to the predetermined region of the storage circuitry 150 when executing the second ultrasound scan. When the information obtained as a result of the reference indicates "0", the processing circuitry 160 controls the transmission and reception circuitry 110 and the B-mode processing circuitry 130, so as to perform the processes using the phase modulation method described above. In contrast, when the information obtained as a result of the reference indicates "1", the processing circuitry 160 controls the transmission and reception circuitry 110 and the B-mode processing circuitry 130, so as to perform the processes using the amplitude modulation method described above.

Further, the letter "D" in FIG. 2 denotes the first scan region in which the first ultrasound scans are performed by using transmission and reception conditions in a color Doppler mode. For example, the letter "D" in FIG. 2 denotes the range in which the ultrasound scans are performed by implementing the high framerate method described above. In other words, in the first ultrasound scans, the ultrasound transmission and reception is performed once with respect to each of the scanning lines, instead of transmitting an ultrasound wave multiple times in the same direction to receive reflected waves multiple times like in a general color Doppler method. As the first ultrasound scans, by performing the ultrasound transmission and reception once with respect to each of the plurality of scanning lines forming the first scan region, the transmission and reception circuitry 110 performs the ultrasound scans based on the method (the high framerate method) by which the blood flow information is obtained while using the reflected waves corresponding to a plurality of frames.

As illustrated in FIG. 2, the transmission and reception circuitry 110, at first, performs a second ultrasound scan on a first sectional region (step S1) and performs a first ultrasound scan on a first scan region (corresponding to one frame) (step S2). After that, the transmission and reception circuitry 110 performs a second ultrasound scan on a second sectional region (step S3) and performs a first ultrasound scan on the first scan region (step S4). Subsequently, the transmission and reception circuitry 110 performs a second ultrasound scan on a third sectional region (step S5) and performs a first ultrasound scan on the first scan region (step S6). After that, the transmission and reception circuitry 110 performs a second ultrasound scan on a fourth sectional region (step S7) and performs a first ultrasound scan on the first scan region (step S8), and the process returns to step S1.

In this situation, as illustrated in FIG. 2, the processing circuitry 160 controlling the first ultrasound scans performed by the transmission and reception circuitry 110 arranges the first ultrasound scans to be performed at regular intervals. In other words, a "point X" on a "given scanning line" in the first scan region is scanned one time each in the first ultrasound scans at steps S2, S4, S6, and S8 in FIG. 2, while the scan intervals are controlled to be "T" that is constant. For example, the processing circuitry 160 arranges the first ultrasound scans to be performed at the regular intervals, by arranging the time periods required by the second ultrasound scans to be equal. For example, the processing circuitry 160 exercises control so that the time periods required by the second ultrasound scans performed at steps S1, S3, S5, and S7 in FIG. 2 to be equal. The processing circuitry 160 arranges the sizes, the number of scanning lines, the density and the depth of the scanning lines to be equal among the sectional regions into which the second scan region was divided. For example, when the numbers of scanning lines are equal, the time periods required by the second ultrasound scans are also equal. The Doppler processing circuitry 140 outputs blood flow information at the "point X" by performing the processes described below on a data sequence ("$X_{n-3}$, $X_{n-2}$, $X_{n-1}$, $X_n$, ..." in FIG. 2) in mutually the same position among frames with respect to the first scan region. According to the method described above, the processing circuitry 160 having a display controlling function updates parts of the tissue image corresponding to the sectional regions at the interval "T", instead of updating the tissue image displayed on the display 103 at an interval "4T".

In a conventional color Doppler process, the "MTI filter process" and the "velocity/dispersion/power estimating process" are performed on a data sequence closed within a packet. For this reason, in the conventional color Doppler process, it is possible to output only one piece of blood flow information for one packet. In contrast, in the color Doppler process performed in the scanning mode using the high framerate method, there is no concept of packets in the scans themselves. For this reason, in the color Doppler process performed in the scanning mode described above, it is possible to arbitrarily change the data length of the data sequence used in the process performed for outputting one piece of blood flow information.

Further, in the color Doppler process performed in the scanning mode described above, it is possible to arrange the data sequence used in the process performed for outputting the blood flow information in a preceding temporal phase to overlap with another data sequence used in the process performed for outputting the blood flow information in the next temporal phase.

This aspect will be explained with reference to FIG. 3. FIG. 3 illustrates an example in which the first scan region and the second scan region have mutually the same scanned range, while the scanned range is formed with eight scanning lines, namely, first to eighth scanning lines. Further, in FIG. 3, the eight scanning lines are marked with the numerals "1, 2, 3, 4, 5, 6, 7, and 8" along the azimuth direction (the array direction of the transducer elements of the ultrasound probe 1). Further, in FIG. 3, the second ultrasound scans are indicated with black solid rectangles, while the first ultrasound scans are indicated with white solid rectangles. FIG. 3 illustrates the example in which the scanned range illustrated in FIG. 2 is scanned in the scanning mode used in the first embodiment. More specifically, FIG. 3 illustrates the example in which the first scan region illustrated in FIG. 2 is formed with the eight scanning lines, while each of the sectional regions obtained by dividing the second scan region, which is the same as the first scan region, into four sections, is formed with two scanning lines.

In the scans illustrated in FIG. 3, a second ultrasound scan is performed on the first scanning line and the second scanning line in the stated order. After the second ultrasound scan is performed on the second scanning line, a first ultrasound scan (the first ultrasound scan for the first time) is performed on the first to the eighth scanning lines in the stated order.

Subsequently, after the first ultrasound scan for the first time has been performed, a second ultrasound scan is performed on the third scanning line and the fourth scanning line in the stated order. After the second ultrasound scan is performed on the fourth scanning line, a first ultrasound scan (the first ultrasound scan for the second time) is performed again on the first to the eighth scanning lines in the stated order.

Subsequently, after a second ultrasound scan is performed on the fifth scanning line and the sixth scanning line in the stated order, a first ultrasound scan (the first ultrasound scan for the third time) is performed again on the first to the eighth scanning lines in the stated order.

Subsequently, after the second ultrasound scan is performed on the seventh scanning line and the eighth scanning line in the stated order, a first ultrasound scan (the first ultrasound scan for the fourth time) is performed again on the first to the eighth scanning lines in the stated order. Also after the first ultrasound scan for the fourth time, the second ultrasound scans and the first ultrasound scans are alternately performed in a similar manner. In other words, in the first embodiment, the transmission and reception circuitry 110 alternately performs the first ultrasound scans on the first scan region and the second ultrasound scans on the parts (the sectional regions) of the second scan region.

In this regard, for instance, an example will be explained in which the data length of the data sequence is set to "4", while the overlapping number of the data sequences between displayed frames is set to "3". In that situation, the Doppler processing circuitry 140 generates Doppler data for the first frame from the reflected-wave data acquired in the first ultrasound scans performed for the first time through the fourth times. In other words, the Doppler processing circuitry 140 generates the Doppler data for the first frame from the reflected-wave data acquired in the first ultrasound scans performed in the four times corresponding to the data length "4" of the data sequence. The Doppler data is data from which the blood flow image data is derived. Further, the processing circuitry 160 generates blood flow image data in the first frame, from the Doppler data for the first frame. Further, the processing circuitry 160 causes the display 103 to display a blood flow image in the first frame represented by the blood flow image data in the first frame.

Subsequently, the Doppler processing circuitry 140 generates Doppler data for the second frame from the reflected-wave data acquired in the first ultrasound scans performed for the second time through the fifth time. In this situation, the reflected-wave data acquired in the first ultrasound scans performed for the second time through the fifth time overlap with the abovementioned reflected-wave data acquired in the first ultrasound scans performed for the first time through the fourth times, by the reflected-wave data acquired in the first ultrasound scans performed for the second time through the fourth time. In other words, the pieces of reflected-wave data overlap each other by the number corresponding to the overlapping number "3".

Further, the blood flow image data in the second frame is generated from the Doppler data for the second frame. After that, the blood flow image in the second frame represented by the blood flow image data in the second frame is displayed on the display 103. Similarly, Doppler data for the third frame is generated from the reflected-wave data acquired in the first ultrasound scans performed for the third time through the sixth time. In other words, when N denotes a positive integer, the Doppler data for an N-th frame is generated from the reflected-wave data acquired in the first ultrasound scans performed for the N-th time through the (N+3)-th time.

In the example in FIG. 3, the second ultrasound scans corresponding to one frame are completed when the first ultrasound scans corresponding to four frames have been completed. The example in FIG. 3 uses a display mode in which, while one frame of the blood flow image is displayed, the images of the four sectional regions (the parts of the tissue image and the parts of the contrast images) into which the second scan region is divided are updated.

Figure 4:
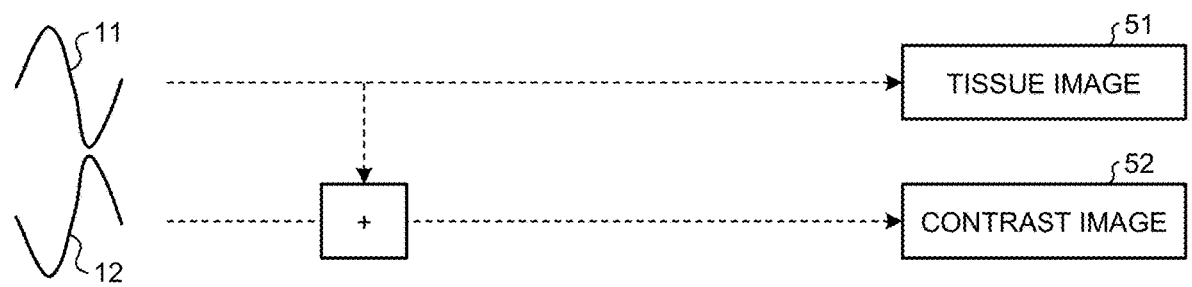
FIG. 4 is a drawing for explaining an example using a phase modulation method in the first embodiment.

Next, an example using the phase modulation method in the second ultrasound scans will be explained. FIG. 4 is a drawing for explaining the example using the phase modulation method in the first embodiment. When the phase modulation method is used, the transmission and reception circuitry 110 causes the ultrasound probe 101 to transmit, with respect to mutually the same scanning line, two types of ultrasound waves having mutually-different polarities, namely an ultrasound wave 11 and an ultrasound wave 12, as illustrated in FIG. 4.

Further, the transmission and reception circuitry 110 generates reflected-wave data based on a reflected wave of the ultrasound wave 11 and reflected-wave data based on a reflected wave of the ultrasound wave 12. Further, the B-mode processing circuitry 130 generates B-mode data (first B-mode data) from which tissue image data is to be derived, by applying an envelope detecting process and/or the like to the reflected-wave data based on the reflected wave of the ultrasound wave 11. Further, the B-mode processing circuitry 130 generate B-mode data (second B-mode data) from which contrast image data is to be derived, by applying an envelope detecting process and/or the like to data obtained by adding the reflected-wave data based on the reflected wave of the ultrasound wave 12 to the reflected-wave data based on the reflected wave of the ultrasound wave 11.

After that, the tissue image generating function 161 generates tissue image data representing a part (a sectional region) of a tissue image 51 on the basis of the first B-mode data. Further, the contrast image generating function 162 generates contrast image data representing a part (a sectional region) of a contrast image 52 rendering non-linear signals from the contrast agent in pictures, on the basis of the second B-mode data.

Figure 5:
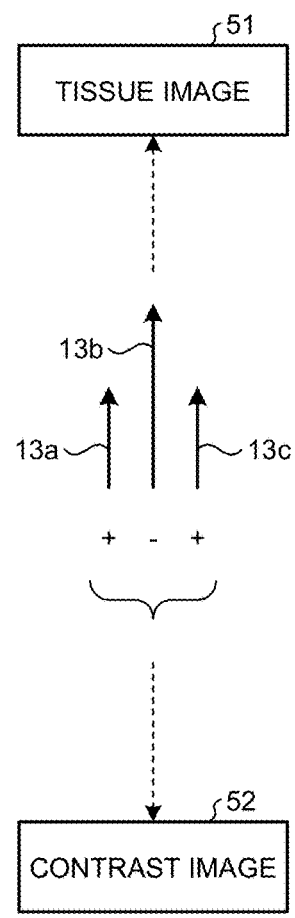
FIG. 5 is a drawing for explaining an example using an amplitude modulation method in the first embodiment.

Next, an example using the amplitude modulation method that can be selected for the second ultrasound scans will be explained. FIG. 5 is a drawing for explaining the example using the amplitude modulation method in the first embodiment. When the amplitude modulation method is used, for example, the transmission and reception circuitry 110 transmits, with respect to mutually the same scanning line, an ultrasound wave 13a of which the amplitude is "0.5", an ultrasound wave 13b of which the amplitude is "1", and an ultrasound wave 13c of which the amplitude is "0.5", in the stated order, as illustrated in FIG. 5. In other words, the transmission and reception circuitry 110 transmits the two types of ultrasound waves, namely, the ultrasound waves 13a and 13c of each of which the amplitude is "0.5" and the ultrasound wave 13b of which the amplitude is "1".

Further, the B-mode processing circuitry 130 performs an adding/subtracting process on the pieces of reflected-wave data based on reflected waves of the three ultrasound waves (the two types of ultrasound waves). More specifically, the B-mode processing circuitry 130 performs the processes described below, where "R1" denotes the reflected-wave data based on the reflected wave of the ultrasound wave 13a, while "R2" denotes the reflected-wave data based on the reflected wave of the ultrasound wave 13b, and "R3" denotes the reflected-wave data based on the reflected wave of the ultrasound wave 13c. For example, the B-mode processing circuitry 130 generates B-mode data (second B-mode data) from which contrast image data is to be derived, by applying an envelope detecting process and/or the like to data resulting from an adding/subtracting process "R1−R2+R3". Further, the B-mode processing circuitry 130 generates B-mode data (first B-mode data) from which tissue image data is to be derived, by applying an envelope detecting process and/or the like to the reflected-wave data "R2" based on the reflected wave of the ultrasound wave 13b.

After that, the tissue image generating function 161 generates tissue image data representing a part (a sectional region) of the tissue image 51, on the basis of the first B-mode data. Further, the contrast image generating function 162 generates contrast image data representing a part (a sectional region) of the contrast image 52 rendering non-linear signals from the contrast agent in pictures, on the basis of the second B-mode data.

In other words, in the examples using either the phase modulation method or the amplitude modulation method, the tissue image data is generated by using a part of the reflected-wave data acquired in the second ultrasound scans, which are scans for acquiring the contrast image data. Consequently, according to the present embodiment, it is possible to acquire the contrast image and the tissue image, by simply performing the single second ultrasound scan.

Figure 6:
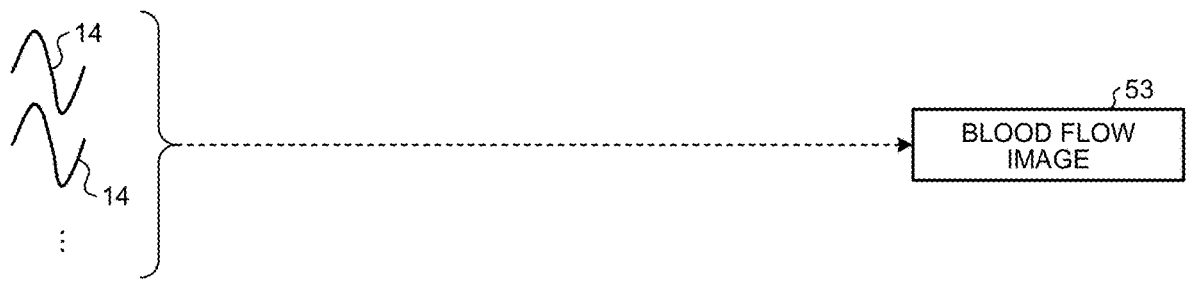
FIG. 6 is a drawing for explaining one example of the first ultrasound scans according to the first embodiment.

Next, one example of the first ultrasound scans will be explained. FIG. 6 is a drawing for explaining the one example of the first ultrasound scans according to the first embodiment.

In the first ultrasound scan, the transmission and reception circuitry 110 performs the ultrasound transmission and reception only once with respect to each of the scanning lines, via the ultrasound probe 101. More specifically, in the first ultrasound scan, the transmission and reception circuitry 110 transmits an ultrasound wave 14 once with respect to each of the plurality of scanning lines structuring the first scan region and receives a reflected wave of the ultrasound wave 14. Further, with respect to each of the scanning lines, the transmission and reception circuitry 110 generates reflected-wave data based on the reflected wave of the ultrasound wave 14. Further, the transmission and reception circuitry 110 repeatedly performs the process of generating reflected-wave data in this manner, as many times as a plurality of frames. After that, the Doppler processing circuitry 140 estimates blood flow information on the basis of the reflected-wave data based on the reflected waves of the ultrasound wave 14 corresponding to the plurality of frames. After that, the Doppler processing circuitry 140 generates Doppler data indicating the estimated blood flow information. Subsequently, on the basis of the Doppler data, the processing circuitry 160 generates blood flow image data representing a blood flow image 53.

Next, an example of a method for generating an MTI filter matrix according to the first embodiment will be explained. At first, the Doppler processing circuitry 140 calculates a correlation matrix of the scanned range, from a data sequence of successive pieces of reflected-wave data in mutually the same position acquired by repeatedly implementing a scanning mode in which the ultrasound transmission and reception is performed once with respect to each of the scanning lines in the first scan region formed by the plurality of scanning lines.

More specifically, the Doppler processing circuitry 140 calculates a correlation matrix "$R_{xx}$" by using Expression (1) presented below.

$$R_{xx} = \frac{1}{M} \sum_{m=1}^{M} x_m x_m^H \quad (1)$$

In Expression (1), "$x_m$" denotes a column vector expressing a data sequence in a certain position "m". The length of the column vector "$x_m$" is the data length used for the estimation calculation of the Doppler data (blood flow information) in one frame. For example, in the example in FIG. 3, "L" is equal to "4". Further, in Expression (1), "$x_m^H$" denotes a transposed matrix of a matrix obtained by calculating complex conjugates of the elements of "$x_m$".

In this situation, the position "m" is the position of a sampling point set in the entire space subject to the high framerate ultrasound scans. The position "m" is indicated in a two-dimensional coordinate system for two-dimensional scans and is indicated in a three-dimensional coordinate system for three-dimensional scans. Further, in Expression (1), "M" denotes the total number of positions "m".

In other words, by using Expression (1), the Doppler processing circuitry 140 calculates an auto-correlation matrix of the data sequence for each of the plurality of sampling points and further calculates an average of the auto-correlation matrices of the plurality of sampling points. Thus, the Doppler processing circuitry 140 calculates a correlation matrix of the first scan region. From Expression (1), the correlation matrix "$R_{xx}$" is a matrix having L rows and L columns. As mentioned above, it is possible to arbitrarily change the data length "L" of the data sequence used for calculating the correlation matrix. The data sequence used for calculating the correlation matrix may be set so as to overlap each other between displayed frames.

Further, the Doppler processing circuitry 140 calculates eigenvalues of the correlation matrix and eigenvectors corresponding to the eigenvalues. In other words, the Doppler processing circuitry 140 calculates L sets of eigenvalues and eigenvectors from the correlation matrix "$R_{xx}$". Further, the Doppler processing circuitry 140 sets a matrix "V" by arranging the L eigenvectors on the basis of the magnitudes of the eigenvalues. Further, the Doppler processing circuitry 140 calculates a matrix obtained by reducing the rank of the matrix "V", as an MTI filter matrix for suppressing clutter components. By using the L eigenvectors as L column vectors, the Doppler processing circuitry 140 obtains a matrix in which the L column vectors are arranged in descending order of the eigenvalues thereof as the matrix "V". Further, by using Expression (2) presented below, the Doppler processing circuitry 140 calculates an MTI filter matrix "W".

$$W = V \begin{pmatrix} 0 & & & \\ & 0 & & \\ & & \ddots & \\ & & & 1 \\ & & & & 1 \end{pmatrix} V^H \quad (2)$$

In Expression (2), "$V^H$" denotes a complex conjugate transposed matrix of "V". Further, on the right-hand side of Expression (2), the matrix placed between "V" and "$V^H$" is a diagonal matrix having L rows and L columns. From Expression (2), the MTI filter matrix "W" is a matrix having L rows and L columns. In this situation, the number by which the rank is reduced is determined by how many of the diagonal elements of the diagonal matrix having the L rows and the L columns are arranged to be "0". The number by which the rank is reduced will hereinafter be referred to as a "rankcut number".

A column vector (an eigenvector) having a larger eigenvalue corresponds to a clutter component having a smaller frequency shift under the Doppler effect, i.e., having a lower moving speed, in a Doppler scanned range. In other words, the principal component of signal changes in the frame direction (the time direction) corresponds to clutter components. From Expression (2), a matrix is calculated by cutting the rank of the matrix "V", by cutting as many components as the rankcut number starting with components having larger eigenvalues. Further, an inverse transform is performed on the matrix, by using "$V^H$". From Expression (2), it is possible to obtain the MTI filter matrix "W" that functions as a high-pass filter for eliminating movement components (the clutter components) of the tissue.

In this situation, for example, the Doppler processing circuitry 140 determines the value of the rankcut number, on the basis of a pre-set value or a value designated by the operator. The adaptive MTI filter has thus been generated. In other words, the Doppler processing circuitry 140 is configured to obtain the data sequence acquired in the first ultrasound scan performed multiple times with respect to the positions in the first scan region and to generate the adaptive MTI filter on the basis of the data sequence. Further, the Doppler processing circuitry 140 is configured to obtain the blood flow information by inputting the data sequence to the generated adaptive MTI filter. After that, the blood flow image generating function 163 is configured to generate the blood flow image data on the basis of the blood flow information obtained by the Doppler processing circuitry 140.

As explained above, the transmission and reception circuitry 110 is configured to perform the second ultrasound scans (contrast-purpose ultrasound scans) to acquire the contrast signals from the patient P and the first ultrasound scans (blood-flow-purpose ultrasound scans) to acquire the blood flow signals. Further, the tissue image generating function 161 is configured to generate the tissue image data indicating the tissue shape on the basis of the signals acquired in the second ultrasound scans. Further, the contrast image generating function 162 is configured to generate the contrast image data on the basis of a contrast signal that is a signal of a harmonic component acquired from the patient P. Further, the blood flow image generating function 163 is configured to generate the blood flow image data on the basis of the blood flow signals estimated by performing the filtering process to eliminate the principal component of the signal changes in the frame direction, on the signal of the harmonic component acquired from the patient P. In this situation, the contrast image data is image data in which pixel values corresponding to the contrast signals are assigned to certain positions (pixel positions) in the scan region. Further, the blood flow image data is image data in which pixel values corresponding to the blood flow signals are assigned to certain positions (pixel positions) in the scan region.

In other words, the contrast image generating function 162 is configured to generate the contrast image data on the basis of the contrast signals acquired from the patient for whom the contrast agent is administered. Further, the blood flow image generating function 163 is configured to generate the blood flow image data on the basis of the blood flow signals estimated by performing the filtering process on the contrast signals.

The above description is merely an example, and the present disclosure is not limited to the above description. For instance, although FIG. 3 illustrates the example in which the first scan region and the second scan region have mutually the same scanned range, possible embodiments are not limited to this example. For instance, it is sufficient when the first scan region and the second scan region overlap each other at least partially. In other words, the transmission and reception circuitry 110 is configured to perform the contrast-purpose ultrasound scans to acquire the contrast signals from the first scan region of the patient P and the blood-flow-purpose ultrasound scans to acquire the blood flow signals from the second scan region that overlaps with the first scan region at least partially.

On the basis of the contrast image data and the blood flow image data, the identifying function 164 is configured to identify a first region having contrast signals but not having blood flow signals, within a Region of Interest (ROI). For example, on the basis of a difference between the contrast image data and the blood flow image data, the identifying function 164 identifies the first region. Further, the identifying function 164 is configured to identify a second region having contrast signals and blood flow signals. Further, the identifying function 164 is configured to identify a third region having a blood flow speed higher than a threshold value, within a region having blood flow signals. Further, the identifying function 164 is configured to identify a fourth region having a blood flow speed lower than a threshold value, within a region having blood flow signals.

Figure 7:
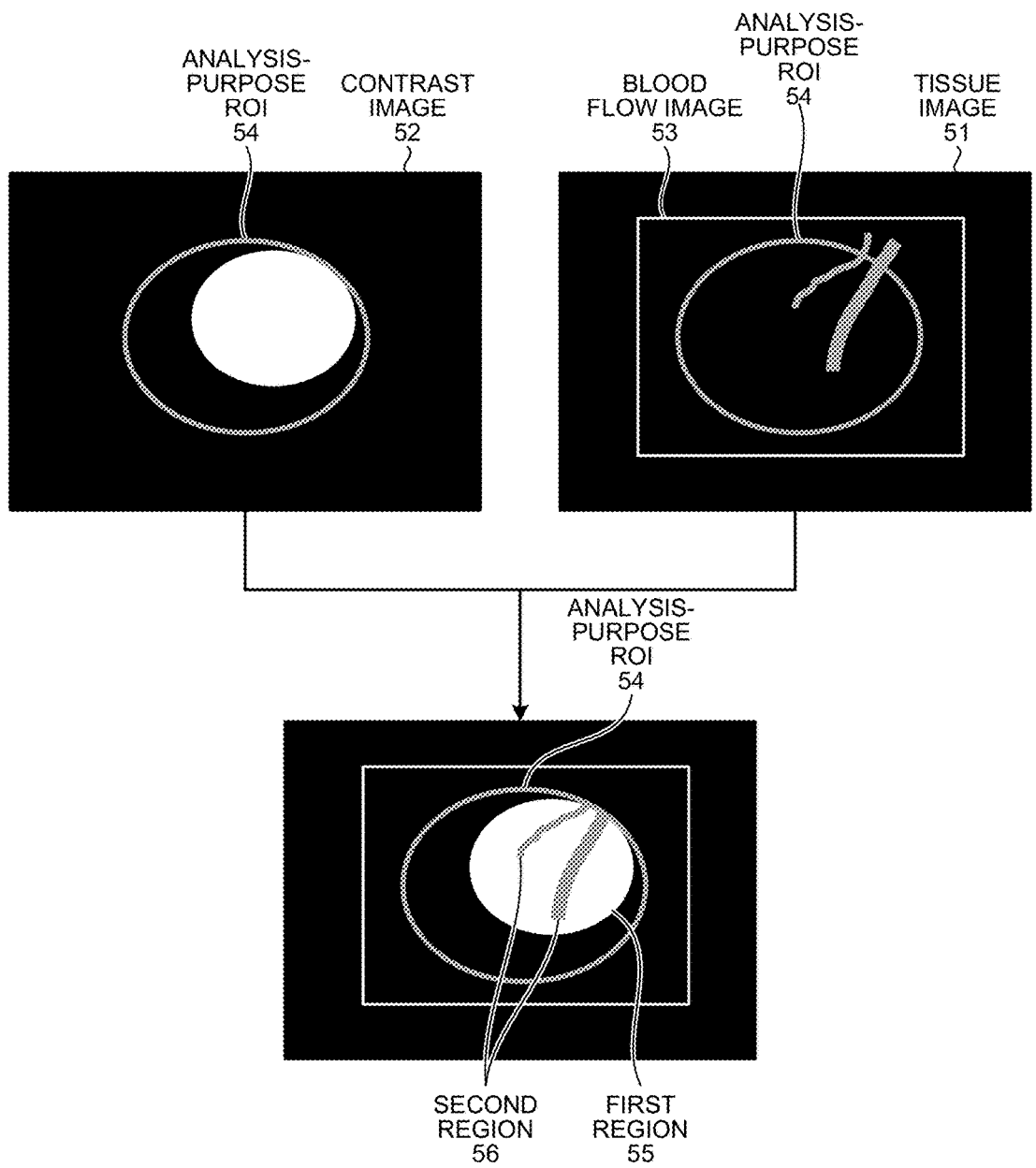
FIG. 7 is a drawing for explaining processes performed by an identifying function according to the first embodiment.
Figure 8:
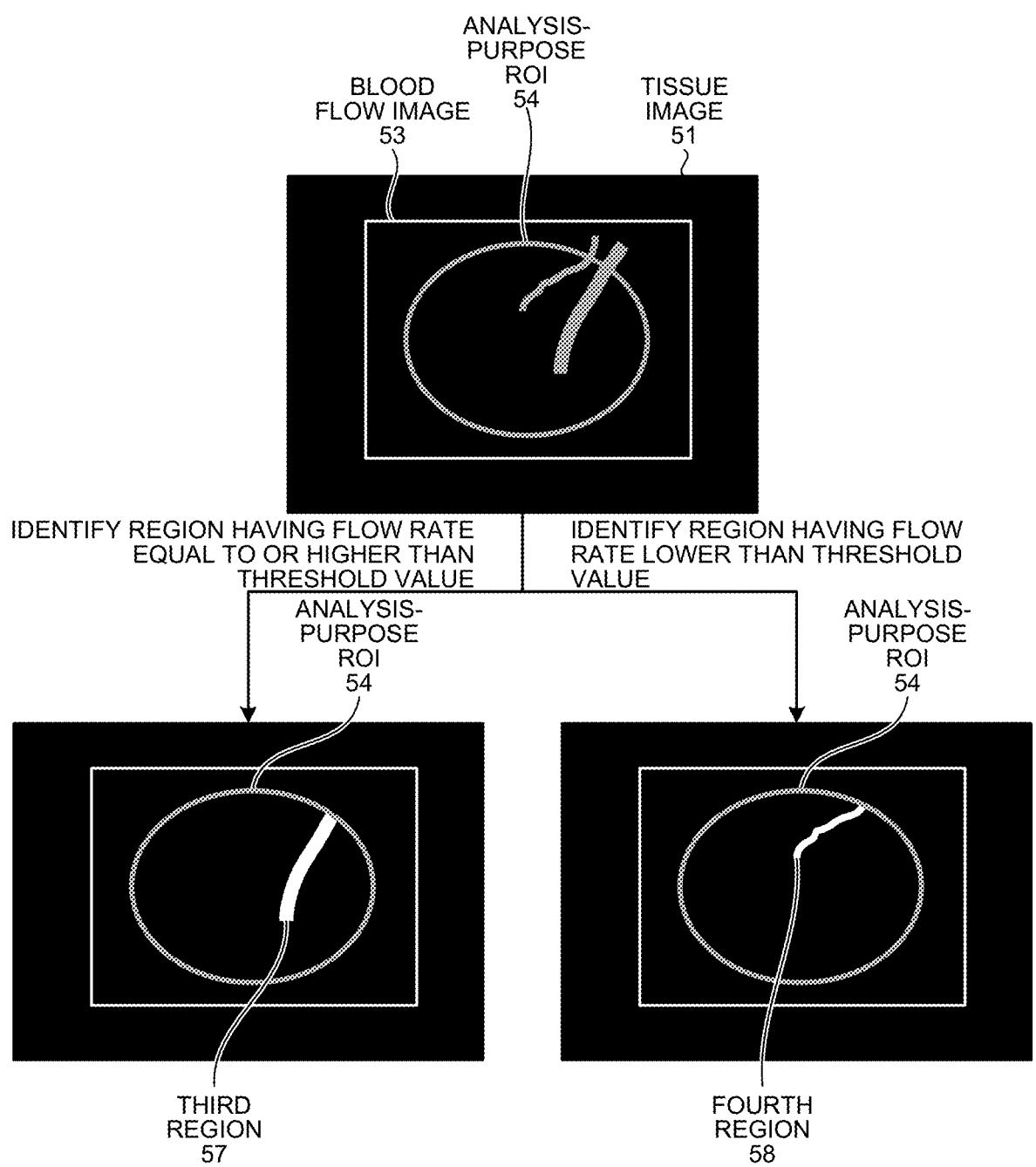
FIG. 8 is another drawing for explaining the processes performed by the identifying function according to the first embodiment.

Processes performed by the identifying function 164 according to the first embodiment will be explained, with reference to FIGS. 7 and 8. FIGS. 7 and 8 are drawings for explaining the processes performed by the identifying function 164 according to the first embodiment. FIG. 7 illustrates an example in which the identifying function 164 identifies the first region and the second region. FIG. 8 illustrates an example in which the identifying function 164 identifies the third region and the fourth region. In FIGS. 7 and 8, the blood flow image 53 exhibits blood flows in a display-purpose ROI set on the inside of the tissue image 51. For the sake of convenience in illustration, the blood flow image 53 exhibits two blood vessels by using homogeneous hatching; however, it is desirable, in actuality, to assign colors (pixel values) corresponding to the blood flow directions or the blood flow speeds (the flow rates).

The upper section of FIG. 7 illustrates the contrast image 52 and a superimposed image in which the blood flow image 53 is superimposed on the tissue image 51. In this situation, the tissue image 51 renders, for example, the contour of a tumor. The identifying function 164 is configured to set an analysis-purpose ROI 54 along the contour of the tumor rendered in the tissue image 51. The analysis-purpose ROI 54 may manually be set by the operator or may automatically be set by using a segmentation process or the like.

Further, the identifying function 164 is configured to perform an identifying process, by using contrast image data and blood flow image data acquired in mutually the same temporal phase. For example, by subtracting the blood flow image data from the contrast image data, the identifying function 164 identifies a first region 55 having contrast signals but not having blood flow signals, within the analysis-purpose ROI 54. The region is illustrated as a white solid region in the bottom section of FIG. 7.

Further, on the basis of the contrast image data and the blood flow image data, the identifying function 164 identifies second regions 56 having contrast signals and blood flow signals, within the analysis-purpose ROI 54. The regions are illustrated as regions with hatching, in the bottom section of FIG. 7.

Further, on the basis of the blood flow image data, the identifying function 164 identifies a third region having a blood flow speed higher than a first threshold value, within the analysis-purpose ROI 54. For example, the first threshold value is set to a value between the flow rate of an artery and the flow rate of a vein. In other words, the third region identified by the identifying function 164 indicates the position of the artery.

Further, for example, on the basis of the blood flow image data, the identifying function 164 identifies a fourth region having a blood flow speed lower than a second threshold value, within the analysis-purpose ROI 54. For example, the second threshold value is set to a value between the flow rate of an artery and the flow rate of a vein. In other words, the fourth region identified by the identifying function 164 indicates the position of the vein. The second threshold value may have the same value as, or may have a different value from, the first threshold value used for identifying the position of the artery.

As explained above, on the basis of the various types of ultrasound image data in mutually the same temporal phase, the identifying function 164 is configured to identify the various types of regions (the first region 55, the second region 56, the third region 57, and the fourth region 58). Further, on the basis of the various types of ultrasound image data in another temporal phase, the identifying function 164 identifies the first region 55, the second region 56, the third region 57, and the fourth region 58 in the temporal phase. Accordingly, with respect to each of all the temporal phases, the identifying function 164 identifies the first region 55, the second region 56, the third region 57, and the fourth region 58.

The above description is merely an example, and the present disclosure is not limited to the above description. For instance, although FIGS. 7 and 8 illustrate the example having an extremely small impact of noise and artifacts, it is also acceptable, when impacts of noise and artifacts are present, to identify a region having pixel values (power values) within a predetermined range, by setting a threshold value. For example, the identifying function 164 may perform the identifying process described above after eliminating the impacts of the noise and the artifacts by setting at least one threshold value, for the purpose of excluding pixels having extremely high pixel values and/or for the purpose of excluding pixels having pixel values lower than a certain level.

Further, for instance, although FIGS. 7 and 8 illustrate the example in which the four regions, namely, the first, the second, the third, and the fourth regions, are identified, possible embodiments are not limited to this example. For instance, the identifying function 164 may perform the identifying process described above on at least one arbitrary region selected from among the first, the second, the third, and the fourth regions.

Further, for example, although the above description refers to the example in which the identifying process is performed with respect to all the temporal phases in which the ultrasound image data was acquired, possible embodiments are not limited to this example. For instance, the identifying function 164 may perform the identifying process described above, with respect to arbitrarily-selected one or more temporal phases.

Further, for example, although FIGS. 7 and 8 illustrate the example in which the various types of regions are identified by the processes performed on the image data, possible embodiments are not limited to this example. For instance, the identifying function 164 is also capable of identifying the various types of regions on the basis of information (distribution information of various types of signals in the scan region) before being converted into the image data. In other words, the identifying function 164 is configured to identify the regions.

The output controlling function 165 is configured to output information related to the identified first region. For example, as the output information, the output controlling function 165 causes the first region to be displayed by at least one of the contrast image data, the blood flow image data, and the tissue image data.

For example, the output controlling function 165 causes the display 103 to display the various types of regions (the first region, the second region, the third region, and the fourth region) identified by the identifying function 164. In that situation, the output controlling function 165 causes the various types of regions to be displayed so as to be distinguishable from other regions. Further, although it is desirable to assign pixel values (power values) or colors (pixel values) corresponding to the blood flow directions or the blood flow speeds (the flow rates) to the regions, it is also possible to display only the outlines of the regions. Further, although it is desirable to arrange the regions to be displayed as being superimposed on ultrasound images such as the tissue image 51, the contrast image 52, and the blood flow image 53, it is also possible to display the regions as images rendering only the regions.

Further, for example, the output controlling function 165 is configured to display, as the output information, a graph indicating chronological changes of brightness values in the various types of regions (the first region, the second region, the third region, and the fourth region). Further, the output controlling function 165 is configured to display, as the output information, the area ratio of each of the various types of regions to a predetermined region.

Figure 9:
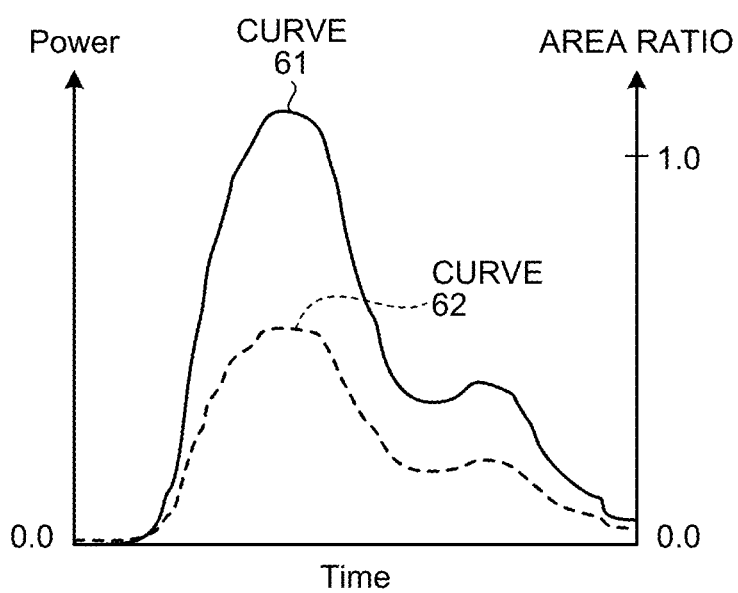
FIG. 9 is a drawing for explaining processes performed by an output controlling function according to the first embodiment.
Figure 10:
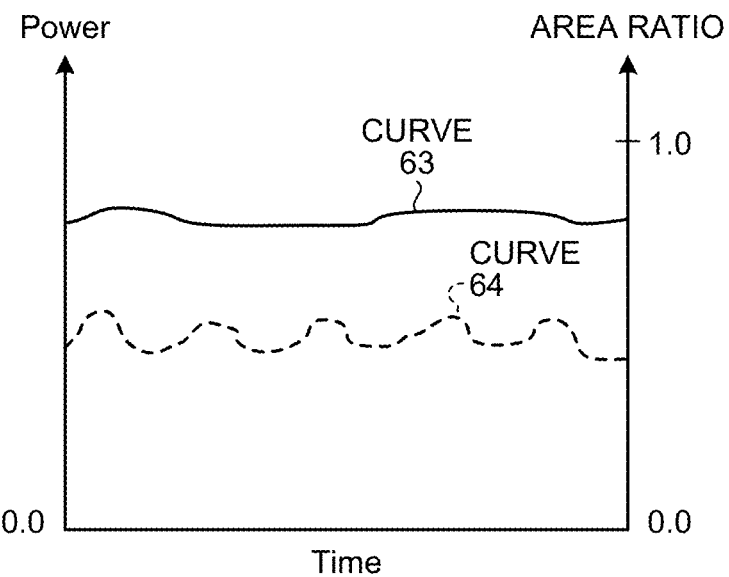
FIG. 10 is another drawing for explaining the processes performed by the output controlling function according to the first embodiment.
Figure 11:
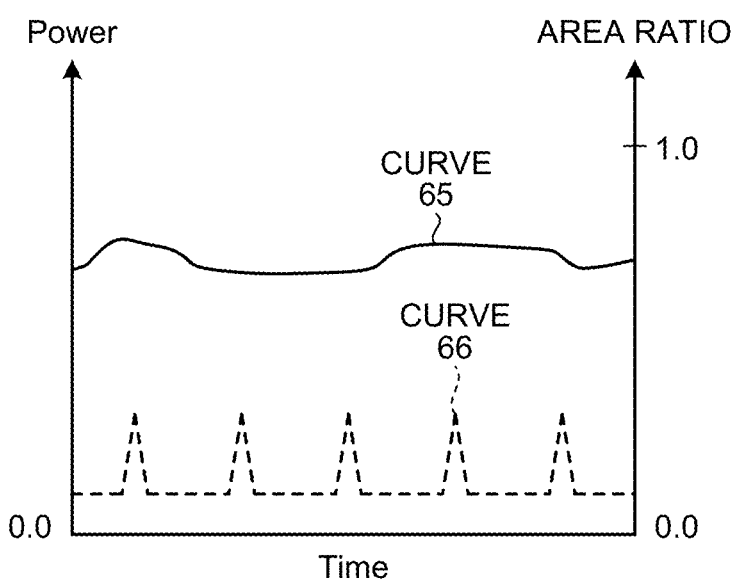
FIG. 11 is yet another drawing for explaining the processes performed by the output controlling function according to the first embodiment.

Processes performed by the output controlling function 165 according to the first embodiment will be explained, with reference to FIGS. 9, 10, and 11. FIGS. 9, 10, and 11 are drawings for explaining the processes performed by the output controlling function 165 according to the first embodiment. In FIGS. 9, 10, and 11, the horizontal axis corresponds to time, whereas the vertical axis corresponds to power values or area ratios. Because the areas of the pixels are constant, the explanations below are based on "area=the number of pixels".

As illustrated in FIG. 9, for example, the output controlling function 165 displays, as the output information, a graph (a Time Intensity Curve [TIC]) indicating chronological changes of pixel values in the first region. More specifically, with respect to each of the temporal phases, the output controlling function 165 calculates an average value of the power values of the plurality of pixels contained in the first region. Further, the output controlling function 165 displays a curve 61 by plotting the calculated average value of the power values in the graph in FIG. 9.

Further, for example, as the output information, the output controlling function 165 displays the area ratio of the first region to the analysis-purpose ROI 54. More specifically, with respect to each of the temporal phases, the output controlling function 165 calculates the area ratio of the first region to the analysis-purpose ROI 54. In this situation, when "Px1" denotes the area (the number of pixels) of the analysis-purpose ROI 54, whereas "Px2" denotes the area of the first region, the output controlling function 165 calculates the area ratio "Px2/Px1". Further, the output controlling function 165 displays a graph (a curve 62) indicating chronological changes of the area ratio, by plotting the calculated area ratio "Px2/Px1" in the graph in FIG. 9.

The description of FIG. 9 is merely an example, and possible embodiments are not limited to the above description. For instance, although FIG. 9 illustrates the example in which the TIC of the first region is displayed, possible embodiments are not limited to this example. For instance, the output controlling function 165 may display a TIC with respect to each of the regions such as the second region, the third region, the fourth region, a region having blood flow signals in the blood flow image 53, and a region having contrast signals in the contrast image 52. Further, as TICs, the output controlling function 165 may plot, not only the average values of the pixel values contained in each of the regions, but also values calculated by using other calculating methods. For example, the output controlling function 165 is also capable of plotting pixel values of the center pixel of each of the regions as a TIC.

Further, for example, although FIG. 9 illustrates the example in which the area ratio "Px2/Px1" of the first region to the analysis-purpose ROI 54 is displayed, possible embodiments are not limited to this example. For instance, the output controlling function 165 may display, as the output information, the area ratio of the second region to the region having contrast signals (the white solid region in the contrast image 52 in FIG. 7). In this situation, when "Px3" denotes the area of the region having the contrast signals, whereas "Px4" denotes the area of the second region, the output controlling function 165 calculates the area ratio "Px4/Px3". Further, the output controlling function 165 displays a graph indicating chronological changes of the area ratio, by plotting the calculated area ratio "Px4/Px3" in the graph in FIG. 9.

As illustrated in FIG. 10, on the basis of the blood flow image data, the output controlling function 165 identifies the region having the blood flow signals within the analysis-purpose ROI 54. Further, as the output information, the output controlling function 165 displays a TIC (a curve 63) of the region having the blood flow signal within the analysis-purpose ROI 54. Because the process of displaying the TIC is the same as that explained with reference to FIG. 9, the explanation thereof will be omitted.

Further, as the output information, the output controlling function 165 displays the area ratio of the second region to the analysis-purpose ROI 54. In this situation, when "Px4" denotes the area of the second region in the analysis-purpose ROI 54, the output controlling function 165 calculates the area ratio "Px4/Px1". Further, the output controlling function 165 displays a graph (a curve 64) indicating chronological changes of the area ratio, by plotting the calculated area ratio "Px4/Px1" in the graph in FIG. 10.

In this situation, the curve 64 is displayed because it is possible to determine whether the imaged object is an artery or a vein on the basis of periodicity of the curve. In other words, because the thickness of an artery periodically changes in accordance with pulsation, the area of the region having the blood flow signals in the blood flow image 53 also periodically changes in accordance with the pulsation. Accordingly, by checking the periodicity of the curve 64, the operator is able to easily determine whether the blood vessel is an artery or a vein. In particular, the determination can easily be made in a later phase of the contrast enhancement period.

The description of FIG. 10 is merely an example, and possible embodiments are not limited to the above description. For instance, as the output information, the output controlling function 165 is also capable of displaying the area ratio of the region having the contrast signals (the white solid region in the contrast image 52 in FIG. 7) to the analysis-purpose ROI 54. In that situation, the output controlling function 165 calculates the area ratio "Px3/Px1". Further, the output controlling function 165 displays a graph indicating chronological changes of the area ratio, by plotting the calculated area ratio "Px3/Px1" in the graph in FIG. 10.

Further, for instance, although FIG. 10 illustrates the example in which the operator visually recognizes the periodicity of the curve 64, possible embodiments are not limited to this example. For instance, the output controlling function 165 is also capable of automatically determining whether the blood vessel is an artery or a vein, by analyzing the periodicity of the curve 64. For example, the output controlling function 165 is able to determine that the blood vessel is an artery in any of the following situations: when the difference between a maximum value and a minimum value of the curve 64 is equal to or larger than a threshold value; when a maximum value of differential values of the curve 64 is equal to or larger than a threshold value; and when periodicity is recognized by a Fourier analysis or the like.

As illustrated in FIG. 11, as the output information, the output controlling function 165 displays a TIC (a curve 65) of the third region. Because the process of displaying the TIC is the same as that explained with reference to FIG. 9, the explanation thereof will be omitted.

Further, as the output information, the output controlling function 165 displays the area ratio of the third region to the second region. In this situation, when "Px5" denotes the area of the third region, the output controlling function 165 calculates the area ratio "Px5/Px4". Further, the output controlling function 165 displays a graph (a curve 66) indicating chronological changes of the area ratio, by plotting the calculated area ratio "Px5/Px4" in the graph in FIG. 11.

In this situation, the curve 66 is displayed because it is possible to determine whether the imaged object is an artery or a vein on the basis of periodicity of the curve. In other words, because arteries are pulsatile, the blood flow amount of a certain flow rate or higher periodically changes in accordance with pulsation. For this reason, the area ratio of the third region to the second region also periodically changes in accordance with the pulsation. Accordingly, by viewing the periodicity of the curve 66, the operator is able to easily determine whether the blood vessel is an artery or a vein. In particular, the determination can easily be made in a later phase of the contrast enhancement period.

The description of FIG. 11 is merely an example, and possible embodiments are not limited to the above description. For instance, as the output information, the output controlling function 165 is also capable of displaying the area ratio of the fourth region to the second region. In this situation, when "Px6" denotes the area of the fourth region, the output controlling function 165 calculates the area ratio "Px6/Px4". Further, the output controlling function 165 displays a graph indicating chronological changes of the area ratio, by plotting the calculated area ratio "Px6/Px4" in the graph in FIG. 11.

Further, for instance, although FIG. 11 illustrates the example in which the operator visually recognizes the periodicity of the curve 66, possible embodiments are not limited to this example. For instance, the output controlling function 165 is also capable of automatically determining whether the blood vessel is an artery or a vein, by analyzing the periodicity of the curve 66. For example, the output controlling function 165 is able to determine that the blood vessel is an artery in any of the following situations: when the difference between a maximum value and a minimum value of the curve 66 is equal to or larger than a threshold value; when a maximum value of differential values of the curve 66 is equal to or larger than a threshold value; and when periodicity is recognized by a Fourier analysis or the like.

As explained above, as the output information, the output controlling function 165 displays the graphs indicating the chronological changes of the brightness values in the various types of regions (the first region, the second region, the third region, and the fourth region) and the area ratios of each of the various types of regions to the prescribed regions. In this situation, the output controlling function 165 is able to simultaneously display two or more of the plurality of graphs described above. The operator is able to arbitrarily combine any of the graphs to be displayed simultaneously.

Further, for example, the output controlling function 165 is capable of displaying the TICs and the area ratios, not only in the graphs, but also as numerical values. In that situation, the output controlling function 165 may display a list of numerical values in different temporal phases or may display a numerical value at a point in time (in a temporal phase) or an average value of numerical values in a certain time period.

In other words, the output controlling function 165 is configured to output information indicating a region where the contrast agent is stagnant within the region of interest. For example, on the basis of the contrast image data and the blood flow image data, the output controlling function 165 outputs the information indicating the region where the contrast is stagnant within the region of interest.

Figure 12:
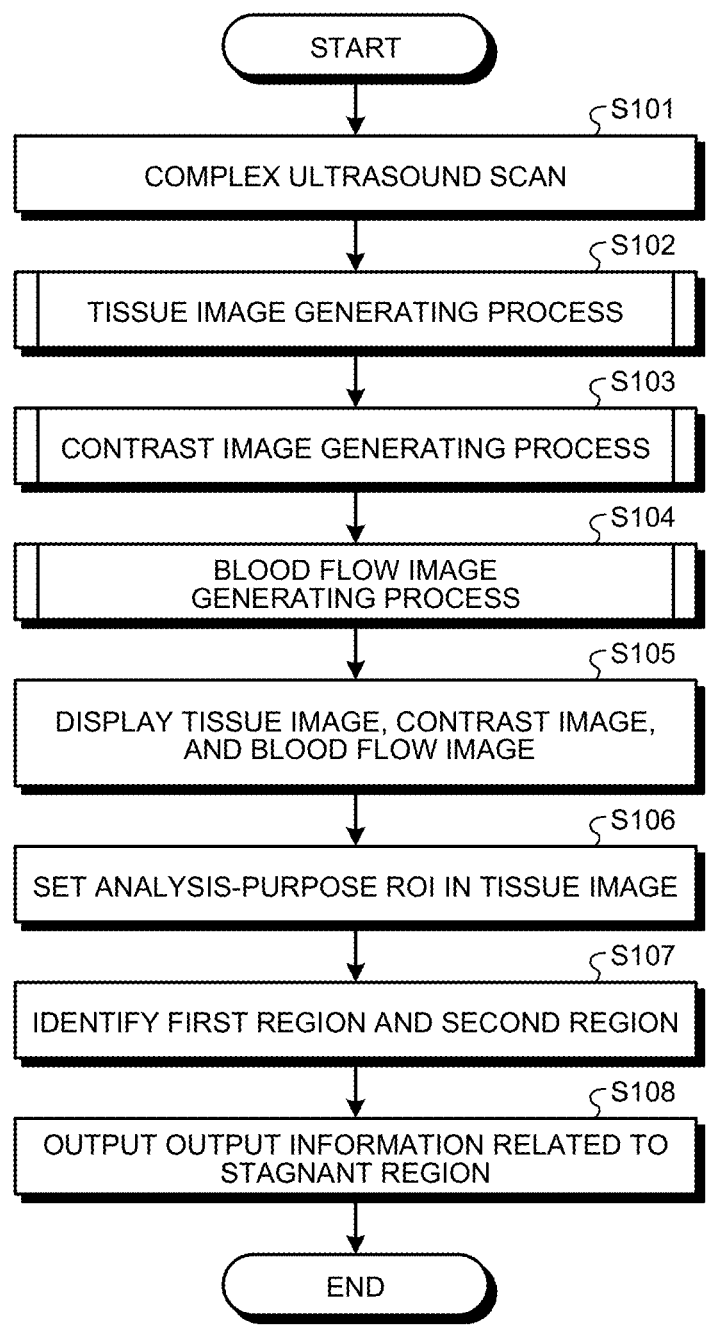
FIG. 12 is a flowchart illustrating a processing procedure performed by the ultrasound diagnosis apparatus according to the first embodiment.

Next, a processing procedure performed by the ultrasound diagnosis apparatus 1 according to the first embodiment will be explained, with reference to FIG. 12. FIG. 12 is a flowchart illustrating the processing procedure performed by the ultrasound diagnosis apparatus 1 according to the first embodiment. The processing procedure in FIG. 12 is started as being triggered by an image taking start request input by the operator, for example.

Figure 13:
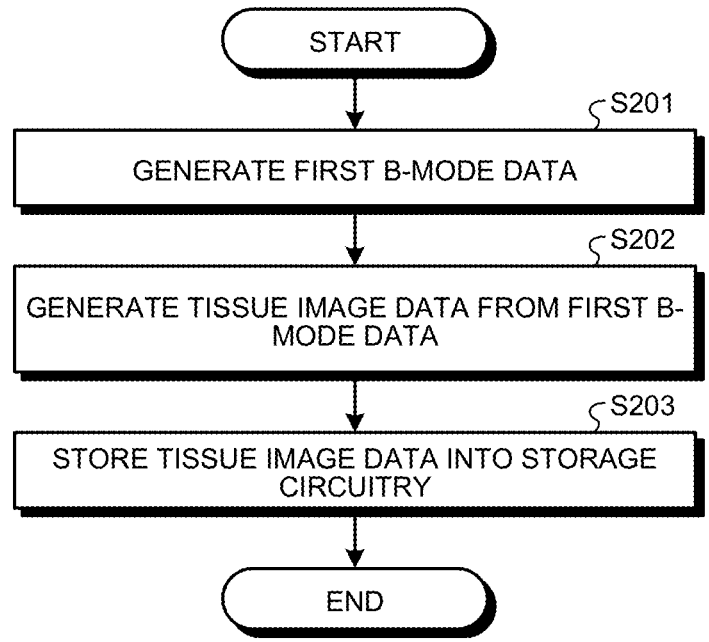
FIG. 13 is a flowchart illustrating a processing procedure in a tissue image generating process according to the first embodiment.

As illustrated in FIG. 12, the transmission and reception circuitry 110 performs a complex ultrasound scan (step S101). Further, the tissue image generating function 161 performs a tissue image generating process (step S102). Next, a processing procedure in the tissue image generating process in FIG. 12 will be explained, with reference to FIG. 13. FIG. 13 is a flowchart illustrating the processing procedure in the tissue image generating process according to the first embodiment.

As illustrated in FIG. 13, the B-mode processing circuitry 130 generates the first B-mode data from which tissue image data is to be derived (step S201). Further, the tissue image generating function 161 generates the tissue image data from the first B-mode data (step S202). After that, the tissue image generating function 161 stores the tissue image data into the storage circuitry 150 (step S203), and the tissue image generating process is ended.

Figure 14:
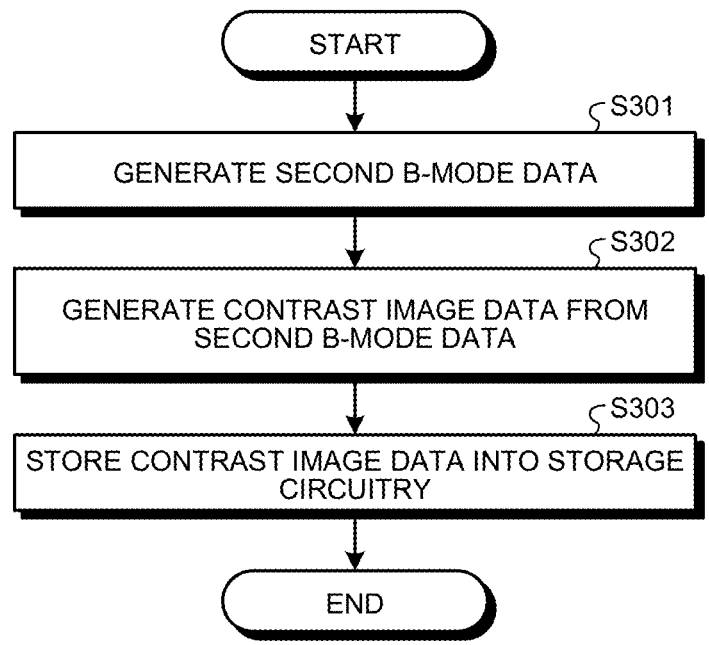
FIG. 14 is a flowchart illustrating a processing procedure in a contrast image generating process according to the first embodiment.

Further, the contrast image generating function 162 performs a contrast image generating process (step S103). Next, a processing procedure in the contrast image generating process in FIG. 12 will be explained, with reference to FIG. 14. FIG. 14 is a flowchart illustrating the processing procedure in the contrast image generating process according to the first embodiment.

As illustrated in FIG. 14, the B-mode processing circuitry 130 generates the second B-mode data from which contrast image data is to be derived (step S301). Further, the contrast image generating function 162 generates the contrast image data from the second B-mode data (step S302). After that, the contrast image generating function 162 stores the contrast image data into the storage circuitry 150 (step S303), and the contrast image generating process is ended.

Figure 15:
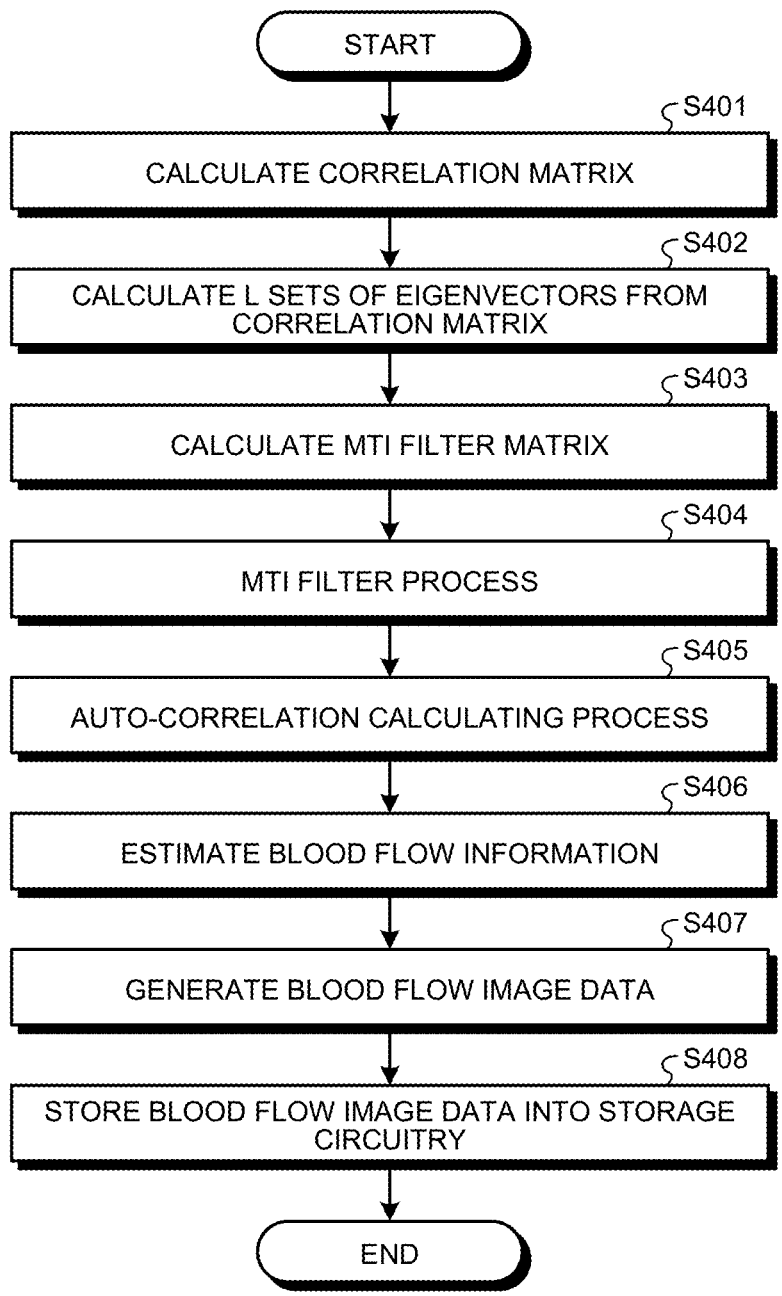
FIG. 15 is a flowchart illustrating a processing procedure in a blood flow image generating process according to the first embodiment.

Further, the blood flow image generating function 163 performs a blood flow image generating process (step S104). Next, a processing procedure in the blood flow image generating process in FIG. 12 will be explained, with reference to FIG. 15. FIG. 15 is a flowchart illustrating the processing procedure in the blood flow image generating process according to the first embodiment.

As illustrated in FIG. 15, the Doppler processing circuitry 140 calculates a correlation matrix of the first scan region (step S401). Further, the Doppler processing circuitry 140 calculates L sets of eigenvalues and eigenvectors from the correlation matrix (step S402).

After that, the Doppler processing circuitry 140 calculates an MTI filter matrix on the basis of the L sets of eigenvalues and eigenvectors (step S403). Further, the Doppler processing circuitry 140 performs the MTI filter process on pieces of reflected-wave data in mutually the same position corresponding to the data length (step S404). After that, by using output data output from the MTI filter process, the Doppler processing circuitry 140 performs the auto-correlation calculating process (step S405). Further, the Doppler processing circuitry 140 estimates blood flow information from a result of the auto-correlation calculating process and generates Doppler data indicating the blood flow information (step S406).

Further, the blood flow image generating function 163 generates blood flow image data from the Doppler data indicating the blood flow information (step S407). In other words, the blood flow image generating function 163 generates a blood flow image based on results of the first ultrasound scan performed multiple times. Further, the blood flow image generating function 163 stores the blood flow image data into the storage circuitry 150 (step S408), and the blood flow image generating process is ended.

Further, the output controlling function 165 displays the tissue image, the contrast image, and the blood flow image (step S105). Further, the identifying function 164 sets an analysis-purpose ROI in the tissue image (step S106). For example, by receiving an input of setting the analysis-purpose ROI in the tissue image from the operator, the identifying function 164 receives the setting of the analysis-purpose ROI.

Further, the output controlling function 165 identifies various types of regions (step S107). For example, the output controlling function 165 identifies the first region, the second region, the third region, and the fourth region. After that, the output controlling function 165 outputs the output information (step S108).

The description of FIGS. 12 to 15 is merely an example, and possible embodiments are not limited to the above description. For instance, the processing procedures illustrated in FIGS. 12 to 15 are merely examples, and it is possible to arbitrarily change the order as long as no conflict occurs in specifics of the processing. For instance, the tissue image generating process, the contrast image generating process, and the blood flow image generating process illustrated in FIG. 12 do not necessarily have to be performed in the order indicated in the drawing and may be performed in an arbitrary order or may be performed simultaneously in parallel processing.

The ultrasound diagnosis apparatus 1 according to the first embodiment has thus been explained. In the first embodiment, as explained above, it is possible to analyze the stagnant location of the contrast agent. For example, the ultrasound diagnosis apparatus 1 is configured to identify the first region corresponding to the stagnant location of the contrast agent and to output the various types of output information related to the identified first region. Accordingly, the ultrasound diagnosis apparatus 1 is able to analyze the stagnant location of the contrast agent.

Further, the ultrasound diagnosis apparatus 1 displays the first region, the second region, the third region, and the fourth region so as to be recognizable. As a result, the operator is able to easily recognize visually the stagnant location of the contrast agent and the surrounding region thereof and to easily understand hemodynamics.

Further, the ultrasound diagnosis apparatus 1 is configured to display the area ratios of the regions to another region, the regions namely being the first region, the second region, the third region, and the fourth region. The area ratios serve as indices of homogeneity. For example, when the area ratio "Px2/Px1" is high, it is considered that the contrast agent stagnant location in a tumor has high homogeneity. As a result, the operator is able to easily understand homogeneity of the contrast agent stagnant location in the tumor. It is therefore possible to provide assistance in determining whether a tumor occurring in a breast is benign or malignant.

Second Embodiment

In addition to the functions of the ultrasound diagnosis apparatus 1 according to the first embodiment, the ultrasound diagnosis apparatus 1 according to a second embodiment has a function of generating vector image data on the basis of vectors expressing chronological movements of contrast agent bubbles. As a result, in addition to the analyses explained in the first embodiment, the ultrasound diagnosis apparatus 1 according to the second embodiment is able to output information related to moving vectors of the contrast agent bubbles.

The processing circuitry 160 according to the second embodiment further includes a tracking image generating function configured to generate tracking image data on the basis of the vectors expressing the chronological movements of the contrast agent bubbles. The tracking image generating function is an example of the tracking image generating unit.

For example, by using a technique described in Japan Application Publication No. 2018-015155, the processing circuitry 160 calculates moving vectors of individual microbubbles contained in the contrast agent. Further, the processing circuitry 160 outputs information related to the calculated moving vectors.

More specifically, among a plurality of contrast images 52 arranged in a time series generated by the contrast image generating function 162, the processing circuitry 160 identifies positions of contrast agent bubbles in each of two contrast images 52 corresponding to two temporal phases. Further, on the basis of the positions of the contrast agent bubbles identified in each of the two contrast images 52, the processing circuitry 160 calculates moving vectors expressing the movements of the contrast agent bubbles. Further, the processing circuitry 160 generates the tracking image data indicating the calculated moving vectors. After that, the output controlling function 165 displays the generated tracking image data.

Figure 16:
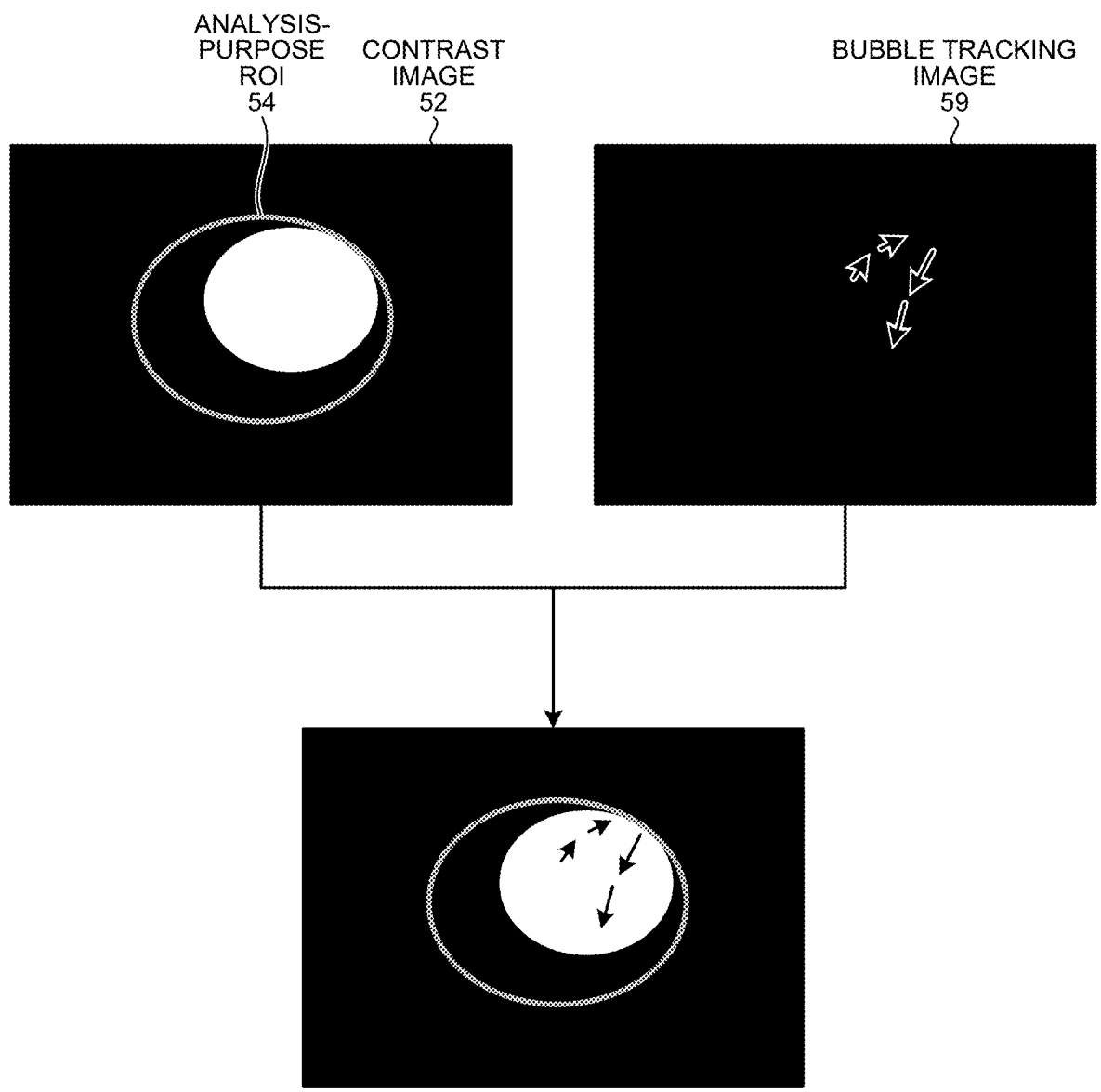
FIG. 16 is a drawing for explaining a process performed by processing circuitry according to a second embodiment.

Processes performed by the processing circuitry 160 according to the second embodiment will be explained, with reference to FIG. 16. FIG. 16 is a drawing for explaining the processes performed by the processing circuitry 160 according to the second embodiment. In FIG. 16, a bubble tracking image 59 corresponds to the tracking image data indicating the moving vectors of the bubbles.

As illustrated in FIG. 16, the processing circuitry 160 generates the bubble tracking image 59. For example, the arrows rendered in the bubble tracking image 59 indicate movements of the contrast agent bubbles. More specifically, the directions of the arrows rendered in the bubble tracking image 59 indicate moving directions of the contrast agent bubbles in that temporal phase. Further, the lengths of the arrows rendered in the bubble tracking image 59 indicate the moving speeds of the contrast agent bubbles in that temporal phase.

For example, the output controlling function 165 causes the display 103 to display an image obtained by superimposing the bubble tracking image 59 on the contrast image 52. Further, the output controlling function 165 displays a graph indicating chronological changes of an average speed of the contrast agent bubbles in the first region. For example, the output controlling function 165 calculates an average speed of the moving vectors rendered in the bubble tracking image 59 and plots the calculated average speed in a graph. Further, the output controlling function 165 displays a graph indicating chronological changes of an average speed of the contrast agent bubbles in a region having blood flow signals.

Accordingly, the ultrasound diagnosis apparatus 1 is able to display, as a reference, the moving vectors of the contrast agent bubbles in the region having the contrast signals. As a result, from within the region having the contrast signals, the operator is able to determine a region where no moving vectors of the contrast agent bubbles are present or where the moving speeds of the contrast agent bubbles are sufficiently small (i.e., the region where the magnitudes of the moving vectors are smaller than a threshold value) as a stagnant location of the contrast agent and is thus able to analyze the stagnant location. In this situation, the "region where the magnitudes of the moving vectors are smaller than a threshold value" may be rephrased as a "region where the moving amounts of the contrast agent bubbles are smaller than a threshold value".

It is desirable to apply the second embodiment to the initial time period of a number of seconds in the first injection in which the inflow amount of the contrast agent is relatively small or to a certain time immediately after the contrast agent in the scanned range is once destructed by a flush (flash). Alternatively, it is desirable to apply the second embodiment to a situation where contrast is enhanced by using a smaller amount of contrast agent than when a normal contrast enhanced echo method is implemented. The reasons is that, when a large amount of contrast agent is used, there is a possibility that the injected contrast agent may not be detected as dots in contrast image data and that the contrast agent may be detected as being contiguous.

In the above description, the example was explained in which the tracking image data is generated by using the contrast image 52 generated by the contrast image generating function 162, i.e., the contrast image data and the tracking image data are generated on the basis of the signals acquired by mutually the same second ultrasound scan; however, possible embodiments are not limited to this example. For instance, to generate the tracking image data, the transmission and reception circuitry 110 may perform a separate ultrasound scan (a tracking-purpose ultrasound scan) different from the first ultrasound scan and the second ultrasound scan described above. When the tracking-purpose ultrasound scan is performed in a temporal phase sufficiently different from those of the first ultrasound scan and the second ultrasound scan, it is desirable to superimpose the generated tracking image data after aligning the position thereof with the contrast image data on the basis of features in the image. Further, when the tracking-purpose ultrasound scan is performed in substantially the same temporal phase as with the first ultrasound scan and the second ultrasound scan, it is desirable to superimpose the tracking image data without the positional alignment.

Further, in the second embodiment, on the basis of the contrast image data and the tracking image data, the identifying function 164 is also capable of identifying, within the region of interest, a region which has contrast signals and in which the magnitudes of the moving vectors are smaller than a threshold value. Further, the output controlling function 165 is configured to output output information related to the identified region.

Further, although FIG. 16 illustrates the example in which the bubble tracking image 59 is superimposed on the contrast image 52, possible embodiments are not limited to this example. For instance, the output controlling function 165 may simultaneously display the bubble tracking image 59 and the contrast image 52 (arranged next to each other). Further, the output controlling function 165 is also capable of displaying the bubble tracking image 59, together with another ultrasound image such as the blood flow image 53.

Other Embodiments

The present disclosure may be carried out in various different modes other than those described in the above embodiments.

An Identifying Process Using Signals

In the above embodiments, the example was explained in which the various types of regions are identified by performing the processes on the image data; however, possible embodiments are not limited to this example. For instance, the identifying function 164 is also capable of identifying the various types of regions, on the basis of information (distribution information of various types of signals in the scan region) before being converted into the image data.

For example, on the basis of the contrast signals and the blood flow signals, the identifying function 164 is capable of identifying the first region having contrast signals but not having blood flow signals, within the analysis-purpose ROI 54. Further, on the basis of the contrast signals and the blood flow signals, the identifying function 164 is capable of identifying the second region 56 having contrast signals and blood flow signals, within the analysis-purpose ROI 54. Further, on the basis of the blood flow signals, the identifying function 164 is capable of identifying the third region having a blood flow speed higher than the first threshold value, within the analysis-purpose ROI 54. Further, on the basis of the blood flow signals, the identifying function 164 is capable of identifying the fourth region having a blood flow speed lower than the second threshold value, within the analysis-purpose ROI 54.

An Image Analyzing Apparatus

Further, in the above embodiments, the examples were explained in which, for instance, the present disclosure is applied to the ultrasound diagnosis apparatus 1; however, possible embodiments are not limited to these examples. For instance, the present disclosure may be applied to a medical information processing apparatus 200. For example, the medical information processing apparatus 200 corresponds to, for example, a work station, a Picture Archiving Communication System (PACS) viewer, or the like. The medical information processing apparatus 200 is an example of the image analyzing apparatus.

Figure 17:
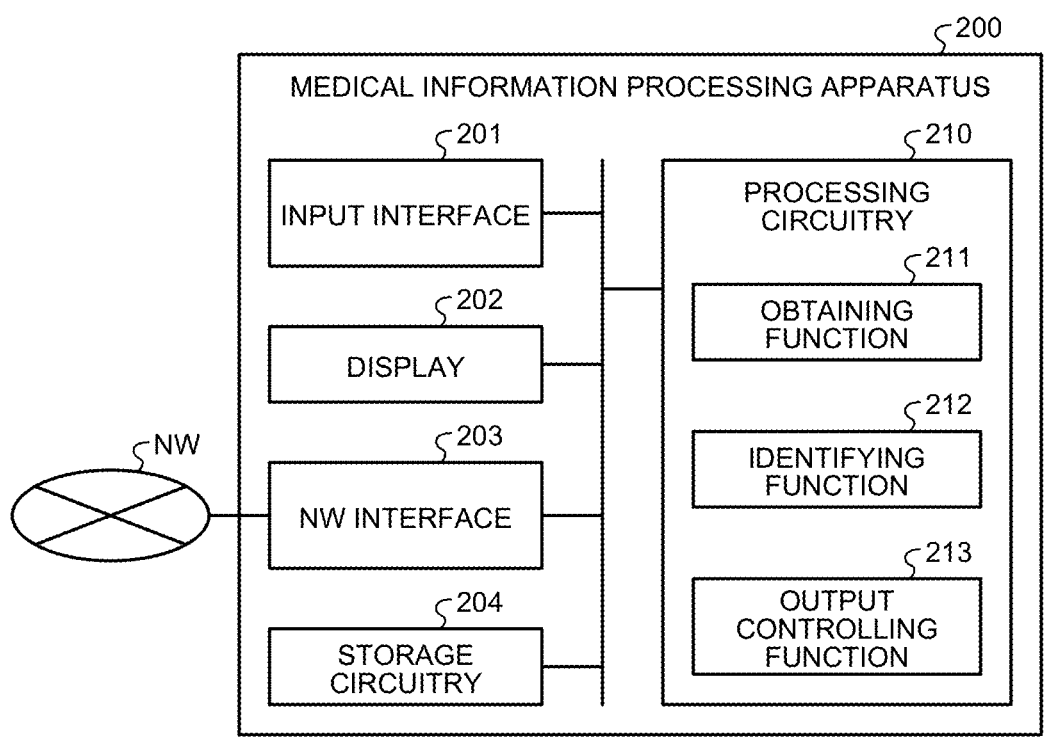
FIG. 17 is a block diagram illustrating an exemplary configuration of a medical information processing apparatus according to another embodiment.

FIG. 17 is a block diagram illustrating an exemplary configuration of the medical information processing apparatus 200 according to another embodiment. As illustrated in FIG. 17, the medical information processing apparatus 200 includes an input interface 201, a display 202, a network (NW) interface 203, storage circuitry 204, and processing circuitry 210. The input interface 201, the display 202, the NW interface 203, storage circuitry 204, and the processing circuitry 210 are connected so as to be able to communicate with one another.

The input interface 201 is an input device such as a mouse, a keyboard, a touch panel, and/or the like, configured to receive various types of instructions and setting requests from an operator. The display 202 is a display configured to display medical images and to display a GUI used by the operator for inputting the various types of setting requests through the input interface 201.

The NW interface 203 is configured to control communication performed between the medical information processing apparatus 200 and external apparatuses. More specifically, the NW interface 203 is configured to receive various types of information from the external apparatuses and to output the received information to the processing circuitry 210. For example, the NW interface 203 is realized by using a network card, a network adaptor, a Network Interface Controller (NIC) or the like.

The storage circuitry 204 is, for example, a Not AND (NAND) flash memory or a Hard Disk Drive (HDD) and is configured to store therein various types of programs for displaying medical image data and GUIs as well as information used by the programs.

The processing circuitry 210 is an electronic device (a processor) configured to control the entirety of processes performed by the medical information processing apparatus 200. The processing circuitry 210 is configured to execute an obtaining function 211, an identifying function 212, and an output controlling function 213. The obtaining function 211, the identifying function 212, and the output controlling function 213 are, for example, recorded in the storage circuitry 204 in the form of computer-executable programs. By reading and executing the programs, the processing circuitry 210 is configured to realize the functions (the obtaining function 211, the identifying function 212, and the output controlling function 213) corresponding to the read programs.

The obtaining function 211 is configured to obtain the contrast image data and the blood flow image data. For example, the obtaining function 211 obtains the contrast image data, tissue image data, and the blood flow image data by receiving the data from an external apparatus (e.g., the ultrasound diagnosis apparatus 1 or a medical image storing apparatus). The identifying function 212 is capable of performing basically the same processes as those performed by the identifying function 164 illustrated in FIG. 1. The output controlling function 213 is capable of performing basically the same processes as those performed by the output controlling function 165 illustrated in FIG. 1. Accordingly, the medical information processing apparatus 200 is able to analyze stagnant locations of the contrast agent.

The description of FIG. 17 is merely an example, and possible embodiments are not limited to the above description. For instance, the medical information processing apparatus 200 may include functions corresponding to the tissue image generating function 161, the contrast image generating function 162, and the blood flow image generating function 163. In that situation, the obtaining function 211 is able to obtain reflected-wave data from which pieces of image data are to be derived, from the ultrasound diagnosis apparatus 1.

Further, the medical information processing apparatus 200 according to the other embodiment is configured to generate the contrast image data on the basis of the contrast signal being a signal of the harmonic component acquired from the patient to whom a contrast agent is administered. Further, the medical information processing apparatus 200 is configured to generate the tracking image data on the basis of the vectors expressing chronological movements of the contrast agent bubbles. On the basis of the contrast image data and the tracking image data, the medical information processing apparatus 200 is configured to identify a region having the contrast signals but having no signals derived from the moving vectors, within the region of interest. In this situation, for example, the signals derived from the moving vectors correspond to the pixel values of the arrows illustrated in the upper right section of FIG. 16. The medical information processing apparatus 200 is configured to output the output information related to the identified region. Accordingly, the medical information processing apparatus 200 is able to analyze stagnant locations of the contrast agent.

Further, the medical information processing apparatus 200 according to the other embodiment is configured to generate the blood flow image data on the basis of the blood flow signals estimated by performing the filtering process to eliminate the principal component of signal changes in the frame direction, on the signal of the harmonic component acquired from a patient to whom a contrast agent is administered. The medical information processing apparatus 200 is configured to generate the tracking image data on the basis of the vectors expressing the chronological movements of the contrast agent bubbles. The medical information processing apparatus 200 is configured to display the blood flow image data and the tracking image data. Accordingly, the medical information processing apparatus 200 is configured to display a bubble tracking image indicating the moving vectors of the blood flow in the surroundings of a stagnant location of the contrast agent and is therefore able to analyze the stagnant location of the contrast agent.

Further, the constituent elements of the apparatuses and the devices described above are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

With regard to the processes explained in the above embodiments, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

Further, it is possible to realize the image analyzing methods described in the above embodiments, by causing a computer such as a personal computer or a workstation to execute an image analyzing program prepared in advance. It is possible to distribute the image analyzing program via a network such as the Internet. Further, it is also possible to record the image analyzing program onto a computer-readable recording medium such as a hard disk, a flexible disk (FD), a Compact Disk Read-Only Memory (CD-ROM), a Magneto Optical (MO) disk, a Digital Versatile Disk (DVD), or the like, so that the program is executed as being read from the recording medium by a computer.

According to at least one of the embodiments described above, it is possible to analyze the stagnant location of the contrast agent.

While a number of embodiments of the present invention have been described, these embodiments are presented by way of examples only, and are not intended to limit the scope of the invention. These embodiments may be carried out in a variety of other forms. Various omissions, substitutions, and changes may be made without departing from the gist of the invention. These embodiments and variations thereof are covered by the invention defined in the accompanying claims and the equivalents thereof, in the same manner as those embodiments and the variations would fall within the scope and the gist of the invention.

What is claimed is:

1. An image analyzing apparatus, comprising:
processing circuitry configured to
generate contrast image data based on a contrast signal acquired from an examined subject to whom a contrast agent is administered;
generate blood flow image data based on a blood flow signal estimated by performing a filtering process on the contrast signal;
identify a stagnant region of the contrast agent where the contrast agent is present and the blood flow is absent in a region of interest, by subtracting the blood flow image data from the contrast image data; and
output information indicating the identified region.

2. The image analyzing apparatus according to claim 1, wherein the processing circuitry is further configured to identify, as the region, a region having the contrast signal but not having the blood flow signal within the region of interest.

3. The image analyzing apparatus according to claim 1, wherein
the region is a first region having the contrast signals but not having the blood flow signals, and
the processing circuitry is further configured to identify a second region having both the contrast signal and the blood flow signal, based on the contrast image data and the blood flow image data.

4. The image analyzing apparatus according to claim 1, wherein the processing circuitry is further configured to perform a contrast-purpose ultrasound scan to acquire the contrast signal from a first scan region of the examined subject and to perform a blood-flow-purpose ultrasound scan to acquire the blood flow signal from a second scan region overlapping with the first scan region at least partially.

5. The image analyzing apparatus according to claim 1, wherein the processing circuitry is further configured to generate tracking image data based on a vector expressing a chronological movement of a contrast agent bubble, and display the tracking image data.

6. The image analyzing apparatus according to claim 1, wherein the processing circuitry is further configured to cause, as the information, the region to be displayed by at least one of the contrast image data and the blood flow image data.

7. The image analyzing apparatus according to claim 1, wherein the processing circuitry is further configured to display, as the information, a graph indicating a chronological change of a pixel value in the region.

8. The image analyzing apparatus according to claim 1, wherein the processing circuitry is further configured to display, as the information, an area ratio of the region to the region of interest.

9. The image analyzing apparatus according to claim 1, wherein the processing circuitry is further configured to display, as the information, an area ratio of a second region having the contrast signal and the blood flow signal to a region having the contrast signal.

10. The image analyzing apparatus according to claim 1, wherein the processing circuitry is further configured to display, as the information, an area ratio of a third region having a blood flow speed higher than a threshold value, to a second region having the contrast signal and the blood flow signal.

11. The image analyzing apparatus according to claim 1, wherein the processing circuitry is further configured to display, as the information, an area ratio of a fourth region having a blood flow speed lower than a threshold value, to a second region having the contrast signal and the blood flow signal.

12. The image analyzing apparatus according to claim 1, wherein the region is a first region, and the processing circuitry is further configured to simultaneously display two or more graphs selected from among the following, as the information:

a graph indicating a chronological change of a pixel value in a region having a contrast signal of the contrast image data;

a graph indicating a chronological change of a pixel value in a region having a blood flow signal of the blood flow image data;

a graph indicating a chronological change of a pixel value in a third region having a blood flow speed higher than a threshold value;

a graph indicating a chronological change of a pixel value in a fourth region having a blood flow speed lower than a threshold value;

a graph indicating a chronological change of an area ratio of a region having the contrast signal to the region of interest;

a graph indicating a chronological change of an area ratio of a region having the blood flow signal to the region of interest;

a graph indicating a chronological change of an area ratio of the first region to the region of interest;

a graph indicating a chronological change of an area ratio of a second region having the contrast signal and the blood flow signal, to a region having the contrast signal;

a graph indicating a chronological change of an area ratio of a region having a blood flow speed higher than a threshold value, to a second region having the contrast signal and the blood flow signal;

a graph indicating a chronological change of an area ratio of a region having a blood flow speed lower than a threshold value, to a second region having the contrast signal and the blood flow signal;

a graph indicating a chronological change of an average speed of contrast agent bubbles in the region of interest;

a graph indicating a chronological change of an average speed of contrast agent bubbles in the first region; and a graph indicating a chronological change of an average speed of contrast agent bubbles in a region having the blood flow signal.

13. The image analyzing apparatus according to claim 1, the image analyzing apparatus being an ultrasound diagnosis apparatus.

14. The image analyzing apparatus according to claim 1, wherein the contrast signal is a signal of a harmonic component acquired from the examined subject to whom the contrast agent is administered.

15. The image analyzing apparatus according to claim 1, wherein the filtering process is a filtering process to eliminate a principal component of a signal change in a frame direction.

16. An image analyzing apparatus, comprising:

processing circuitry configured to generate contrast image data based on a contrast signal acquired from an examined subject to whom a contrast agent is administered;

generate tracking image data indicating a chronological movement of individual contrast agent bubbles; and output, based on the contrast image data and the tracking image data, information indicating a region which has the contrast signal and in which an average speed of the contrast agent bubbles is smaller than a threshold value, within a region of interest.

* * * * *